(12) United States Patent
Raikar et al.

(10) Patent No.: US 9,845,323 B2
(45) Date of Patent: Dec. 19, 2017

(54) 2-(1,3,4-OXADIAZOL-2-YL)-7-OXO-1,6-DIAZABICYCLO[3.2.1]OCTANE DERIVATIVES AND THEIR USE AS ANTIBACTERIAL AGENTS

(71) Applicant: WOCKHARDT LIMITED, Aurangabad 0 (IN)

(72) Inventors: Sanjay Raikar, Aurangabad (IN); Sanjay Kisan Dabhade, Maharashtra (IN); Laxmikant Pavase, Maharashtra (IN); Sachin Bhagwat, Aurangabad (IN); Ravindra Dattatraya Yeole, Maharashtra (IN); Mahesh Vithalbhai Patel, Maharashtra (IN)

(73) Assignee: WOCKHARDT LIMITED, Chikalthana, Aurangabad (IN)

( * ) Notice: Subject to any disclaimer, the term of this patent is extended or adjusted under 35 U.S.C. 154(b) by 0 days.

(21) Appl. No.: 15/108,278

(22) PCT Filed: Jan. 21, 2015

(86) PCT No.: PCT/IB2015/050455
§ 371 (c)(1),
(2) Date: Jun. 24, 2016

(87) PCT Pub. No.: WO2015/110963
PCT Pub. Date: Jul. 30, 2015

(65) Prior Publication Data
US 2016/0297816 A1    Oct. 13, 2016

(30) Foreign Application Priority Data
Jan. 21, 2014  (IN) .......................... 192/MUM/2014

(51) Int. Cl.
| | |
|---|---|
| *C07D 471/08* | (2006.01) |
| *A61K 31/4995* | (2006.01) |
| *A61K 31/439* | (2006.01) |
| *A61K 31/445* | (2006.01) |
| *A61K 31/496* | (2006.01) |
| *A61K 31/546* | (2006.01) |
| *A61K 31/695* | (2006.01) |
| *A61K 45/06* | (2006.01) |
| *C07F 7/18* | (2006.01) |
| *A61K 31/407* | (2006.01) |
| *A61K 31/424* | (2006.01) |

(52) U.S. Cl.
CPC .......... *C07D 471/08* (2013.01); *A61K 31/407* (2013.01); *A61K 31/424* (2013.01); *A61K 31/439* (2013.01); *A61K 31/445* (2013.01); *A61K 31/496* (2013.01); *A61K 31/546* (2013.01); *A61K 31/695* (2013.01); *A61K 45/06* (2013.01); *C07F 7/1856* (2013.01)

(58) Field of Classification Search
None
See application file for complete search history.

(56) References Cited

FOREIGN PATENT DOCUMENTS

| WO | WO2013030735 A1 | 3/2013 |
|---|---|---|
| WO | WO2013149121 A1 | 10/2013 |

OTHER PUBLICATIONS

Burgers Medicinal Chemistry, edited by Manfred E. Wolff, 5th Ed. Part 1, pp. 975-977 (1995).*
Banker et al. "Modern Pharmaceutics", 3rd Ed. p. 596 (1996).*
Testa et al. Pure Appl. Chem. vol. 76, pp. 907-914 (2004).*

* cited by examiner

*Primary Examiner* — Emily Bernhardt
(74) *Attorney, Agent, or Firm* — Bio Intellectual Property Services LLC (BioIPS); O. (Sam) Zaghmout

(57) ABSTRACT

Compounds of Formula (I), their preparation, and use in preventing or treating a bacterial infection are disclosed.

Formula (I)

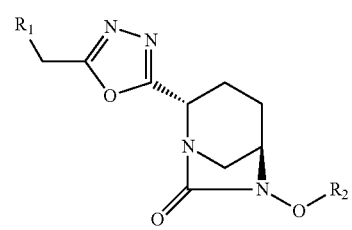

19 Claims, No Drawings

2-(1,3,4-OXADIAZOL-2-YL)-7-OXO-1,6-DIAZABICYCLO[3.2.1]OCTANE DERIVATIVES AND THEIR USE AS ANTIBACTERIAL AGENTS

RELATED PATENT APPLICATIONS

This application claims priority to Indian Patent Application No. 192/MUM/2014 filed on Jan. 21, 2014, the disclosures of which are incorporated herein by reference in its entirety as if fully rewritten herein.

FIELD OF THE INVENTION

The invention relates to nitrogen containing compounds, their preparation and their use in preventing or treating infections.

BACKGROUND OF INVENTION

Emergence of bacterial resistance to known antibacterial agents is becoming a major challenge in treating bacterial infections. One way forward to treat bacterial infections, and especially those caused by resistant bacteria, is to develop newer antibacterial agents that can overcome the bacterial resistant. Coates et al. (*Br. J. Pharmacol.* 2007; 152(8), 1147-1154.) have reviewed novel approaches to developing new antibiotics. However, the development of new antibacterial agents is a challenging task. For example, Gwynn et al. (*Annals of the New York Academy of Sciences,* 2010, 1213: 5-19) have reviewed the challenges in discovery of antibacterial agents.

Several compounds have been described in the prior art for use in treatment of bacterial infections (for example, see Patent Application Nos. PCT/IB2012/054296, PCT/IB2012/054290, US20130225554, PCT/US2010/060923, PCT/EP2010/067647, PCT/US2010/052109, PCT/US2010/048109, PCT/GB 2009/050609, PCT/EP2009/056178, PCT/US2009/041200, PCT/US2013/034562, PCT/US2013/034589, PCT/IB2013/053092 and PCT/IB2012054706). However, there remains a need for potent antibacterial agents for preventing and/or treating bacterial infections, including those caused by bacteria that are resistant to known antibacterial agents.

The inventors have now surprisingly discovered novel nitrogen containing compounds having potent antibacterial activity.

SUMMARY OF THE INVENTION

Accordingly, there are provided nitrogen containing compounds, methods for preparation of these compounds, pharmaceutical compositions comprising these compounds, and method for preventing or treating a bacterial infection in a subject using these compounds.

In one general aspect, there are provided compounds of Formula (I):

Formula (I)

or a stereoisomer or a pharmaceutically acceptable derivative thereof;

wherein:

$R_1$ is:
- (a) $C_1$-$C_6$ alkyl optionally substituted with one or more substituents independently selected from $C_1$-$C_6$ alkyl, halogen, CN, $OR_3$, $NR_3R_4$, $CONR_3R_4$, cycloalkyl, heterocycloalkyl, aryl, or heteroaryl;
- (b) heterocycloalkyl optionally substituted with one or more substituents independently selected from $C_1$-$C_6$ alkyl, halogen, CN, $OR_3$, $NR_3R_4$, or $CONR_3R_4$;
- (c) aryl optionally substituted with one or more substituents independently selected from $C_1$-$C_6$ alkyl, halogen, CN, $OR_3$, $NR_3R_4$, or $CONR_3R_4$; or
- (d) heteroaryl optionally substituted with one or more substituents independently selected from $C_1$-$C_6$ alkyl, halogen, CN, $OR_3$, $NR_3R_4$, or $CONR_3R_4$;

$R_2$ is:
- (a) $SO_3M$,
- (b) $CF_2COOM$,
- (c) CHFCOOM,
- (d) $CH_2COOM$, or
- (e) $CF_3$;

$R_3$ and $R_4$ are each independently:
- (a) hydrogen, or
- (b) $C_1$-$C_6$ alkyl optionally substituted with one or more substitutents independently selected from halogen, CN, OH, O($C_1$-$C_6$ alkyl), NH($C_1$-$C_6$ alkyl), N($C_1$-$C_6$ alkyl)$_2$, CONH($C_1$-$C_6$ alkyl), CON($C_1$-$C_6$ alkyl)$_2$, cycloalkyl, heterocycloalkyl, aryl or heteroaryl;

M is hydrogen or a cation.

In another general aspect, there are provided pharmaceutical compositions comprising a compound of Formula (I) or a stereoisomer or a pharmaceutically acceptable derivative thereof.

In another general aspect, there are provided methods for preventing or treating a bacterial infection in a subject, said methods comprising administering to said subject a compound of Formula (I) or a stereoisomer or a pharmaceutically acceptable derivative thereof.

In yet another general aspect, there are provided methods for preventing or treating a bacterial infection in a subject, said methods comprising administering to said subject a pharmaceutical composition comprising a compound of Formula (I) or a stereoisomer or a pharmaceutically acceptable derivative thereof.

In another general aspect, there are provided pharmaceutical compositions comprising: (a) a compound of Formula (I) or a stereoisomer or a pharmaceutically acceptable derivative thereof, and (b) at least one beta-lacatamse inhibitor or a pharmaceutically acceptable derivative thereof.

In another general aspect, there are provided pharmaceutical compositions comprising: (a) a compound of Formula (I) or a stereoisomer or a pharmaceutically acceptable derivative thereof, and (b) at least one antibacterial agent or a pharmaceutically acceptable derivative thereof.

In another general aspect, there are provided pharmaceutical compositions comprising: (a) a compound of Formula (I) or a stereoisomer or a pharmaceutically acceptable derivative thereof, (b) at least one beta-lacatamse inhibitor or a pharmaceutically acceptable derivative thereof, and (c) at least one antibacterial agent or a pharmaceutically acceptable derivative thereof.

In another general aspect, there are provided methods for preventing or treating a bacterial infection in a subject, said methods comprising administering to said subject a pharmaceutical composition comprising: (a) a compound of Formula (I) or a stereoisomer or a pharmaceutically acceptable derivative thereof, and (b) at least one beta-lactamase inhibitor or a pharmaceutically acceptable derivative thereof.

In another general aspect, there are provided methods for preventing or treating a bacterial infection in a subject, said methods comprising administering to said subject a pharmaceutical composition comprising: (a) a compound of Formula (I) or a stereoisomer or a pharmaceutically acceptable derivative thereof, and (b) at least one antibacterial agent or pharmaceutically acceptable derivative thereof.

In another aspect, there are provided methods for preventing or treating a bacterial infection in a subject, said methods comprising administering to said subject a pharmaceutical composition comprising: (a) a compound of Formula (I) or a stereoisomer or a pharmaceutically acceptable derivative thereof, (b) at least one beta-lactamase inhibitor or pharmaceutically acceptable derivative thereof, and (c) at least one antibacterial agent or a pharmaceutically acceptable derivative thereof.

In another general aspect, there are provided methods for preventing or treating a bacterial infection in a subject, said methods comprising administering to said subject: (a) a compound of Formula (I) or a stereoisomer or a pharmaceutically acceptable derivative thereof, and (b) at least one beta-lactamase inhibitor or pharmaceutically acceptable derivative thereof.

In another general aspect, there are provided methods for preventing or treating a bacterial infection in a subject, said methods comprising administering to said subject: (a) a compound of Formula (I) or a stereoisomer or a pharmaceutically acceptable derivative thereof, and (b) at least one antibacterial agent or pharmaceutically acceptable derivative thereof.

In another general aspect, there are provided methods for preventing or treating a bacterial infection in a subject, said methods comprising administering to said subject: (a) a compound of Formula (I) or a stereoisomer or a pharmaceutically acceptable derivative thereof, (b) at least one beta-lactamase inhibitor or pharmaceutically acceptable derivative thereof, and (c) at least one antibacterial agent or pharmaceutically acceptable derivative thereof.

In another general aspect, there are provided methods for increasing antibacterial effectiveness of an antibacterial agent in a subject, said methods comprising co-administering said antibacterial agent, or a pharmaceutically acceptable derivative thereof, with a compound of Formula (I) or a stereoisomer or a pharmaceutically acceptable derivative thereof.

The details of one or more embodiments of the invention are set forth in the description below. Other features, objects and advantages of the invention will be apparent from the following description including claims.

DETAILED DESCRIPTION OF THE INVENTION

Reference will now be made to the exemplary embodiments, and specific language will be used herein to describe the same. It should nevertheless be understood that no limitation of the scope of the invention is thereby intended. Alterations and further modifications of the inventive features illustrated herein, which would occur to one skilled in the relevant art and having possession of this disclosure, are to be considered within the scope of the invention. It must be noted that, as used in this specification and the appended claims, the singular forms "a", "an", and "the" include plural referents unless the content clearly dictates otherwise. All references including patents, patent applications, and literature cited in the specification are expressly incorporated herein by reference in their entirety.

The inventors have surprisingly discovered novel nitrogen containing compounds having antibacterial properties.

The term "$C_1$-$C_6$ alkyl" as used herein refers to branched or unbranched acyclic hydrocarbon radical with 1 to 6 carbon atoms. Typical non-limiting examples of "$C_1$-$C_6$ alkyl" include methyl, ethyl, n-propyl, iso-propyl, n-butyl, sec-butyl, iso-butyl, tert-butyl, n-pentyl, iso-pentyl, tert-pentyl, neopentyl, sec-pentyl, 3-pentyl, n-hexyl, 2-methylpentyl, 3-methylpentyl, 2,2-dimethylbutyl, 2,3-dimethylbutyl and the like. The "$C_1$-$C_6$ alkyl" may be unsubstituted, or substituted with one or more substituents. Typical, non-limiting examples of such substituents include halogen, alkoxy, CN, SH, COOH, COO$C_1$-$C_6$alkyl, CONH$_2$, OH, NH$_2$, NHCOCH$_3$, cycloalkyl, heterocycloalkyl, heteroaryl, aryl and the like.

The term "cycloalkyl" as used herein refers to three to seven member cyclic hydrocarbon radicals. The cycloalkyl group optionally incorporates one or more double or triple bonds, or a combination of double or triple bonds, but which is not aromatic. Typical, non-limiting examples of cycloalkyl groups include cyclopropyl, cyclobutyl, cyclopentyl, cyclohexyl, and cycloheptyl. The cycloalkyl may be unsubstituted, or substituted with one or more substituents. Typical, non-limiting examples of such substituents include $C_1$-$C_6$ alkyl, halogen, alkoxy, CN, SH, COOH, COO$C_1$-$C_6$alkyl, CONH$_2$, OH, NH$_2$, NHCOCH$_3$, heterocycloalkyl, heteroaryl, aryl, SO$_2$-alkyl, SO$_2$-aryl, OSO$_2$-alkyl, OSO$_2$-aryl and the like.

The term "aryl" as used herein refers to a monocyclic or polycyclic aromatic hydrocarbon. Typical, non-limiting examples of aryl groups include phenyl, naphthyl, anthracenyl, fluorenyl, phenanthrenyl, indenyl and the like. The aryl group may be unsubstituted, or substituted with one or more substituents. Typical, non-limiting examples of such substituents include C1-C6 alkyl, halogen, alkoxy, CN, COOH, CONH$_2$, OH, NH$_2$, NHCOCH$_3$, heterocycloalkyl, heteroaryl, aryl, SO$_2$-alkyl, SO$_2$-aryl, OSO$_2$-alkyl, OSO$_2$-aryl and the like. In some embodiments, the term "aryl" refers to a monocyclic or polycyclic aromatic hydrocarbon radical containing up to 14 ring atoms.

The term "heteroaryl" as used herein refers to a monocyclic or polycyclic aromatic hydrocarbon group wherein one or more carbon atoms have been replaced with heteroatoms selected from nitrogen, oxygen, and sulfur. If the heteroaryl group contains more than one heteroatom, the heteroatoms may be the same or different. Typical, non-limiting example of heteroaryl groups include pyridyl, pyrimidinyl, pyrazinyl, pyridazinyl, triazinyl, furanyl, pyrrolyl, thienyl, oxadiazolyl, thiadiazolyl, tetrazolyl, oxazolyl, thiazolyl, imidazolyl, pyrazolyl, triazonyl, isoxazolyl, oxadiazolyl, oxatriazolyl, isothiazolyl, thiatriazolyl, thiazinyl, oxazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo-pyridazinyl, purinyl, benzofuranyl, isobenzofuranyl, benzothienyl, benzothiophenyl, carbazolyl, benzimidazolyl, benzoxazolyl, benzoisoxazolyl, benzothiazolyl, benzotriazolyl, indolyl, isoindolyl, quinolinyl, isoquinolinyl, acridinyl, naphthothienyl, thianthrenyl, chromenyl, xanthenyl, phenoxathienyl, indolizinyl, indazolyl, phthalazinyl, naphthyridinyl, qinoxalinyl, quinazolinyl, cinnolinyl, pteridinyl, beta-carbolinyl, phenanthridinyl, phenanthrolinyl, phenazinyl, phenothiazinyl, phenoxazinyl and the like. The heteroaryl group may be unsubstituted, or substituted with one or more substituents. Typical, non-limiting examples of such substituents include C1-C6 alkyl, halogen, alkoxy, CN, COOH, $CONH_2$, OH, SH, $SCH_3$, $NH_2$, $NHCOCH_3$, heterocycloalkyl, heteroaryl, aryl, $SO_2$-alkyl, $SO_2$-aryl, $OSO_2$-alkyl, $OSO_2$-aryl and the like. In some embodiments, the term "heteroaryl" refers to a monocyclic or polycyclic aromatic hydrocarbon radical containing up to 14 ring atoms.

The term "heterocycloalkyl" as used herein refers to four to seven member cycloalkyl group containing one or more heteroatoms selected from nitrogen, oxygen or sulfur. The heterocycloalkyl group optionally incorporates one or more double or triple bonds, or a combination of double bonds and triple bonds, but which is not aromatic. Typical, non-limiting example of heterocycloalkyl groups include azetidinyl, pyrrolidinyl, 2-oxo-pyrrolidinyl, imidazolidin-2-one-yl, piperidinyl, oxazinyl, thiazinyl, piperazinyl, piperazin-2,3-dione-yl, morpholinyl, thiomorpholinyl, azepanyl, and the like. The heterocycloalkyl may be unsubstituted, or substituted with one or more substituents. Typical, non-limiting examples of such substituents include $C_1$-$C_6$ alkyl, halogen, alkoxy, CN, COOH, $CONH_2$, OH, $NH_2$, $NHCOCH_3$, heteroaryl, aryl, $SO_2$-alkyl, $SO_2$-aryl, $OSO_2$-aryl and the like.

The term "halogen" or halo as used herein refers to chlorine, bromine, fluorine or iodine.

The term "stereoisomers" as used herein refers to compounds that have identical chemical constitution, but differ with regard to the arrangement of their atoms or groups in space. The compounds of Formula (I) may contain asymmetric or chiral centers and, therefore, exist in different stereoisomeric forms. It is intended, unless specified otherwise, that all stereoisomeric forms of the compounds of Formula (I) as well as mixtures thereof, including racemic mixtures, form part of the present invention. In addition, the present invention embraces all geometric and positional isomers (including cis and trans-forms), as well as mixtures thereof, are embraced within the scope of the invention. In general, a reference to a compound is intended to cover its stereoisomers and mixture of various stereoisomers.

The term "optionally substituted" as used herein means that the substitution is optional and therefore includes both unsubstituted and substituted atoms and moieties. A "substituted" atom or moiety indicates that any hydrogen on the designated atom or moiety can be replaced with a selection from the indicated substituent group, provided that the normal valency of the designated atom or moiety is not exceeded, and that the substitution results in a stable compound.

The term "pharmaceutically acceptable derivative" as used herein refers to and includes any pharmaceutically acceptable salt, pro-drugs, metabolites, esters, ethers, hydrates, polymorphs, solvates, complexes or adducts of a compound described herein which, upon administration to a subject, is capable of providing (directly or indirectly) the parent compound. For example, the term "antibacterial or a pharmaceutically acceptable derivative thereof" includes all derivatives of the antibacterial agent (such as salt, prodrugs, metabolites, esters, ethers, hydrates, polymorphs, solvates, complexes or adducts) which, upon administration to a subject, is capable of providing (directly or indirectly) the antibacterial compound.

The term "pharmaceutically acceptable salt" as used herein refers to one or more salts of a given compound which possesses the desired pharmacological activity of the free compound and which are neither biologically nor otherwise undesirable. In general, the "pharmaceutically acceptable salts" refer to salts that are suitable for use in contact with the tissues of human and animals without undue toxicity, irritation, allergic response and the like, and are commensurate with a reasonable benefit/risk ratio. Pharmaceutically acceptable salts are well known in the art. For example, S. M. Berge, et al. (*J. Pharmaceutical Sciences*, 66; 1-19, 1977), incorporated herein by reference in its entirety, describes various pharmaceutical acceptable salts in details.

In general, the compounds according to the invention contain basic (e.g. nitrogen atoms) as well as acid moieties (e.g. compounds of Formula (I) wherein M is hydrogen). A person of skills in the art would appreciate that such compounds, therefore, can form acidic salts (formed with inorganic and/or organic acids), as well as basic salts (formed with inorganic and/or organic bases). Such salts can be prepared using procedures described in the art. For example, the basic moiety can be converted to its salt by treating a compound with a suitable amount of acid. Typical, non-limiting examples of such suitable acids include hydrochloric acid, trifluoroacetic acid, methanesulphonic acid or the like. Alternatively, the acid moiety may be converted into its salt by treating with a suitable base. Typical non-limiting examples of such bases include sodium carbonate, sodium bicarbonate, potassium carbonate, potassium bicarbonate or the like. In case of compounds containing more than one functional group capable of being converted into salt, each such functional group may be converted to salt independently. For example, in case of compounds containing two basic nitrogen atoms, one of the basic nitrogen can form salt with one acid while the other basic nitrogen can form salt with another acid. Some compounds according to the invention contain both acidic as well as basic moieties, and thus can form inner salts or corresponding zwitterions. In general, all pharmaceutically acceptable salt forms of compound of Formula (I) according to invention including acid addition salts, base addition salts, zwitterions or the like are contemplated to be within the scope of the present invention and are generically referred to as pharmaceutically acceptable salts.

The term "OBn" as used herein refers to benzyloxy.

The term "EDC" as used herein refers to 1-ethyl-3-(3-dimethylamino propyl)carbodiimide.

The term "HOBt" as used herein refers to 1-hydroxybenzotriazole.

The term "Boc" as used herein refers to tert-butyloxycarbonyl

The term "infection" or "bacterial infection" as used herein includes presence of bacteria, in or on a subject, which, if its growth were inhibited, would result in a benefit to the subject. As such, the term "infection" in addition to referring to the presence of bacteria also refers to normal floras, which are not desirable. The term "infection" includes infection caused by bacteria.

The term "treat", "treating" or "treatment" as used herein refers to administering a medicament, including a pharmaceutical composition, or one or more pharmaceutically active ingredients, for prophylactic and/or therapeutic purposes. The term "prophylactic treatment" refers to treating a subject who is not yet infected, but who is susceptible to, or otherwise at a risk of infection (preventing the bacterial infection). The term "therapeutic treatment" refers to administering treatment to a subject already suffering from infection. The terms "treat", "treating" or "treatment" as used herein also refer to administering compositions or one or more of pharmaceutically active ingredients discussed herein, with or without additional pharmaceutically active or inert ingredients, in order to: (i) reduce or eliminate either a bacterial infection or one or more symptoms of the bacterial infection, or (ii) retard the progression of a bacterial infection one or more symptoms of the bacterial infection, or (iii) reduce the severity of a bacterial infection or of one or more symptoms of the bacterial infection, or (iv) suppress the clinical manifestation of a bacterial infection, or (v) suppress the manifestation of adverse symptoms of the bacterial infection.

The term "pharmaceutically effective amount" or "therapeutically effective amount" or "effective amount" as used herein refers to an amount, which has a therapeutic effect or is the amount required to produce a therapeutic effect in a subject. For example, a therapeutically or pharmaceutically effective amount of an antibacterial agent or a pharmaceutical composition is the amount of the antibacterial agent or the pharmaceutical composition required to produce a desired therapeutic effect as may be judged by clinical trial results, model animal infection studies, and/or in vitro studies (e.g. in agar or broth media). The pharmaceutically effective amount depends on several factors, including but not limited to, the microorganism (e.g. bacteria) involved, characteristics of the subject (for example height, weight, sex, age and medical history), severity of infection and the particular type of the antibacterial agent used. For prophylactic treatments, a therapeutically or prophylactically effective amount is that amount which would be effective in preventing a microbial (e.g. bacterial) infection.

The term "administration" or "administering" includes delivery of a composition or one or more pharmaceutically active ingredients to a subject, including for example, by any appropriate methods, which serves to deliver the composition or its active ingredients or other pharmaceutically active ingredients to the site of the infection. The method of administration may vary depending on various factors, such as for example, the components of the pharmaceutical composition or the type/nature of the pharmaceutically active or inert ingredients, the site of the potential or actual infection, the microorganism involved, severity of the infection, age and physical condition of the subject and a like. Some non-limiting examples of ways to administer a composition or a pharmaceutically active ingredient to a subject according to this invention includes oral, intravenous, topical, intrarespiratory, intraperitoneal, intramuscular, parenteral, sublingual, transdermal, intranasal, aerosol, intraocular, intratracheal, intrarectal, vaginal, gene gun, dermal patch, eye drop or mouthwash. In case of a pharmaceutical composition comprising more than one ingredient (active or inert), one of the way of administering such composition is by admixing the ingredients (e.g. in the form of a suitable unit dosage form such as tablet, capsule, solution, powder or like) and then administering the dosage form. Alternatively, the ingredients may also be administered separately (simultaneously or one after the other) as long as these ingredients reach beneficial therapeutic levels such that the composition as a whole provides a synergistic and/or desired effect.

The term "growth" as used herein refers to a growth of one or more microorganisms and includes reproduction or population expansion of the microorganism (e.g. bacteria). The term also includes maintenance of on-going metabolic processes of a microorganism, including the processes that keep the microorganism alive.

The term, "effectiveness" as used herein refers to ability of a treatment or a composition or one or more pharmaceutically active ingredients to produce a desired biological effect in a subject. For example, the term "antibacterial effectiveness" of a composition or an antibacterial agent refers to the ability of the composition or the antibacterial agent to prevent or treat the microbial (e.g. bacterial) infection in a subject.

The term "synergistic" or "synergy" as used herein refers to the interaction of two or more agents so that their combined effect is greater than their individual effects.

The term "antibacterial agent" as used herein refers to any substance, compound or a combination of substances or a combination compounds capable of: (i) inhibiting, reducing or preventing growth of bacteria; (ii) inhibiting or reducing ability of a bacteria to produce infection in a subject; or (iii) inhibiting or reducing ability of bacteria to multiply or remain infective in the environment. The term "antibacterial agent" also refers to compounds capable of decreasing infectivity or virulence of bacteria.

The term "beta-lactam antibacterial agent" as used herein refers to compounds with antibacterial properties and containing a beta-lactam nucleus in their molecular structure.

The term "beta-lactamase" as used herein refers to any enzyme or protein or any other substance that breaks down a beta-lactam ring. The term "beta-lactamase" includes enzymes that are produced by bacteria and have the ability to hydrolyze the beta-lactam ring in a beta-lactam compound, either partially or completely.

The term "beta-lactamase inhibitor" as used herein refers to a compound capable of inhibiting activity of one or more beta-lactamase enzymes, either partially or completely.

The term "Extended spectrum beta-lactamase or ESBL" as used herein includes those beta-lactamase enzymes which are capable of conferring bacterial resistance to the penicillins, first-, second-, and third-generation cephalosporins, and aztreonam by hydrolysis of these antibiotics.

The term "pharmaceutically inert ingredient" or "carrier" or "excipient" refers to a compound or material used to facilitate administration of a compound, for example, to increase the solubility of the compound. Solid carriers include, e.g., starch, lactose, dicalcium phosphate, sucrose, and kaolin. Liquid carriers include, e.g., sterile water, saline, buffers, non-ionic surfactants, and edible oils such as oil peanut and sesame oils. In addition, various adjuvants commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990); Goodman and Gilman's: The Pharmacological Basis of Therapeutics, $8^{th}$ Ed., Pergamon Press., which is incorporated herein by reference in its entirety.

The term "subject" as used herein refers to vertebrate or invertebrate, including a mammal. The term "subject" includes human, animal, a bird, a fish, or an amphibian. Typical, non-limiting examples of a "subject" includes humans, cats, dogs, horses, sheep, bovine cows, pigs, lambs, rats, mice and guinea pigs.

In general, the term "cation" includes H, Na, K, Mg, Ca, $NH_4^+$, $(CH_3CH_2)_3N^+$ etc.

In one general aspect, there are provided compounds of Formula (I):

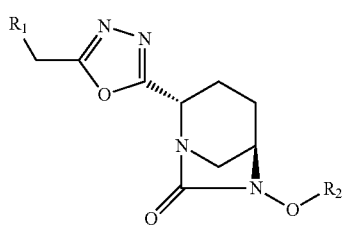

Formula (I)

or a stereoisomer or a pharmaceutically acceptable derivative thereof;
wherein:
$R_1$ is:
(a) $C_1$-$C_6$ alkyl optionally substituted with one or more substituents independently selected from $C_1$-$C_6$ alkyl, halogen, CN, $OR_3$, $NR_3R_4$, $CONR_3R_4$, cycloalkyl, heterocycloalkyl, aryl, or heteroaryl;
(b) heterocycloalkyl optionally substituted with one or more substituents independently selected from $C_1$-$C_6$ alkyl, halogen, CN, $OR_3$, $NR_3R_4$, or $CONR_3R_4$;
(c) aryl optionally substituted with one or more substituents independently selected from $C_1$-$C_6$ alkyl, halogen, CN, $OR_3$, $NR_3R_4$, or $CONR_3R_4$; or
(d) heteroaryl optionally substituted with one or more substituents independently selected from $C_1$-$C_6$ alkyl, halogen, CN, $OR_3$, $NR_3R_4$, or $CONR_3R_4$;
$R_2$ is:
(a) $SO_3M$,
(b) $CF_2COOM$,
(c) CHFCOOM,
(d) $CH_2COOM$, or
(e) $CF_3$;
$R_3$ and $R_4$ are each independently:
(a) hydrogen, or
(b) $C_1$-$C_6$ alkyl optionally substituted with one or more substitutents independently selected from halogen, CN, OH, O($C_1$-$C_6$ alkyl), NH($C_1$-$C_6$ alkyl), N($C_1$-$C_6$ alkyl)$_2$, CONH($C_1$-$C_6$ alkyl), CON($C_1$-$C_6$ alkyl)$_2$, cycloalkyl, heterocycloalkyl, aryl or heteroaryl;
M is hydrogen or a cation.

Typical non-limiting examples of compounds according to the invention include:
(2S,5R)-sulfuric acid mono-[2-(5-azetidin-3-ylmethyl-[1,3,4]-oxadiazol-2-yl)-7-oxo-1,6-diaza-bicyclo[3.2.1] oct-6-yl] ester;
(2S,5R)-sulfuric acid mono-[2-(5-(S)-pyrrolidin-2-ylmethyl-[1,3,4]-oxadiazol-2-yl)-7-oxo-1,6-diaza-bicyclo[3.2.1] oct-6-yl] ester;
(2S,5R)-sulfuric acid mono-[2-(5-piperidin-4-ylmethyl-[1,3,4]-oxadiazol-2-yl)-7-oxo-1,6-diaza-bicyclo[3.2.1] oct-6-yl] ester;
(2S,5R)-sulfuric acid mono[2-(5-(RS)-piperazin-2-ylmethyl-[1,3,4]-oxadiazol-2-yl)-7-oxo-1,6-diaza-bicyclo[3.2.1] oct-6-yl] ester;
(2S,5R)-sulfuric acid mono-[2-(5-benzyl-[1,3,4]-oxadiazol-2-yl)-7-oxo-1,6-diaza-bicyclo[3.2.1] oct-6-yl] ester;
(2S,5R)-sulfuric acid mono-[2-(5-phenyl-ethyl-[1,3,4]-oxadiazol-2-yl)-7-oxo-1,6-diaza-bicyclo[3.2.1] oct-6-yl] ester;
(2S,5R)-sulfuric acid mono-{2-[5-phenyl-propyl)-[1,3,4]-oxadiazol-2-yl]-7-oxo-1,6-diaza-bicyclo[3.2.1] oct-6-yl} ester;
(2S,5R)-sulfuric acid mono-[2-(5-benzhydryl-[1,3,4]-oxadiazol-2-yl)-7-oxo-1,6-diaza-bicyclo[3.2.1] oct-6-yl] ester;
(2S,5R)-sulfuric acid mono-{2-[5-(2,2-diphenyl-ethyl)-[1,3,4]-oxadiazol-2-yl]-7-oxo-1,6-diaza-bicyclo[3.2.1] oct-6-yl} ester;
(2S,5R)-sulfuric acid mono-{2-[5-(4-chloro-benzyl)-[1,3,4]-oxadiazol-2-yl]-7-oxo-1,6-diaza-bicyclo[3.2.1] oct-6-yl} ester;
(2S,5R)-sulfuric acid mono-{2-[5-(4-amino-benzyl)-[1,3,4]-oxadiazol-2-yl]-7-oxo-1,6-diaza-bicyclo[3.2.1] oct-6-yl} ester;
(2S,5R)-sulfuric acid mono-{2-[5-(4-dimethylamino-benzyl)-[1,3,4]-oxadiazol-2-yl]-7-oxo-1,6-diaza-bicyclo[3.2.1] oct-6-yl} ester;
(2S,5R)-sulfuric acid mono-{2-[5-(4-hydroxy-benzyl)-[1,3,4]-oxadiazol-2-yl]-7-oxo-1,6-diaza-bicyclo[3.2.1] oct-6-yl} ester;
(2S,5R)-sulfuric acid mono-{2-[5-(4-methoxy-benzyl)-[1,3,4]-oxadiazol-2-yl]-7-oxo-1,6-diaza-bicyclo[3.2.1] oct-6-yl} ester;
or a stereoisomer or a pharmaceutically acceptable derivative thereof.

In some embodiments, typical non-limiting examples of compounds according to the invention include:
sodium salt of (2S,5R)-sulfuric acid mono-[2-(5-azetidin-3-ylmethyl-[1,3,4]-oxadiazol-2-yl)-7-oxo-1,6-diaza-bicyclo[3.2.1] oct-6-yl] ester;
sodium salt of (2S,5R)-sulfuric acid mono-[2-(5-(S)-pyrrolidin-2-ylmethyl-[1,3,4]-oxadiazol-2-yl)-7-oxo-1,6-diaza-bicyclo[3.2.1] oct-6-yl] ester;
sodium salt of (2S,5R)-sulfuric acid mono-[2-(5-piperidin-4-ylmethyl-[1,3,4]-oxadiazol-2-yl)-7-oxo-1,6-diaza-bicyclo[3.2.1] oct-6-yl] ester;
trifluoroacetic acid salt of (2S,5R)-sulfuric acid mono[2-(5-(RS)-piperazin-2-ylmethyl-[1,3,4]-oxadiazol-2-yl)-7-oxo-1,6-diaza-bicyclo[3.2.1] oct-6-yl] ester;
sodium salt of (2S,5R)-sulfuric acid mono-[2-(5-benzyl-[1,3,4]-oxadiazol-2-yl)-7-oxo-1,6-diaza-bicyclo[3.2.1] oct-6-yl] ester;
sodium salt of (2S,5R)-sulfuric acid mono-[2-(5-phenyl-ethyl-[1,3,4]-oxadiazol-2-yl)-7-oxo-1,6-diaza-bicyclo[3.2.1] oct-6-yl] ester;
sodium salt of (2S,5R)-sulfuric acid mono-{2-[5-(3-phenyl-propyl)-[1,3,4]-oxadiazol-2-yl]-7-oxo-1,6-diaza-bicyclo[3.2.1] oct-6-yl} ester;
sodium salt of (2S,5R)-sulfuric acid mono-[2-(5-benzhydryl-[1,3,4]-oxadiazol-2-yl)-7-oxo-1,6-diaza-bicyclo[3.2.1] oct-6-yl] ester;
sodium salt of (2S,5R)-sulfuric acid mono-{2-[5-(2,2-diphenyl-ethyl)-[1,3,4]-oxadiazol-2-yl]-7-oxo-1,6-diaza-bicyclo[3.2.1] oct-6-yl} ester;
sodium salt of (2S,5R)-sulfuric acid mono-{2-[5-(4-chloro-benzyl)-[1,3,4]-oxadiazol-2-yl]-7-oxo-1,6-diaza-bicyclo[3.2.1] oct-6-yl} ester;
sodium salt of (2S,5R)-sulfuric acid mono-{2-[5-(4-amino-benzyl)-[1,3,4]-oxadiazol-2-yl]-7-oxo-1,6-diaza-bicyclo[3.2.1] oct-6-yl} ester;
sodium salt of (2S,5R)-sulfuric acid mono-{2-[5-(4-dimethylamino-benzyl)-[1,3,4]-oxadiazol-2-yl]-7-oxo-1,6-diaza-bicyclo[3.2.1] oct-6-yl} ester;

sodium salt of (2S,5R)-sulfuric acid mono-{2-[5-(4-hydroxy-benzyl)-[1,3,4]-oxadiazol-2-yl]-7-oxo-1,6-diaza-bicyclo[3.2.1] oct-6-yl} ester;

sodium salt of (2S,5R)-sulfuric acid mono-{2-[5-(4-methoxy-benzyl)-[1,3,4]-oxadiazol-2-yl]-7-oxo-1,6-diaza-bicyclo[3.2.1] oct-6-yl} ester;

or a stereoisomer thereof.

In general, the compounds of the invention can be prepared according to the general procedures given in Schemes 1 and 2. A person of skills in the art would appreciate that the described method can be varied or optimized further to provide the desired and related compounds. In the following procedures, all variables are as defined above.

In some embodiments, there is provided a process for preparation of compounds of Formula (I):

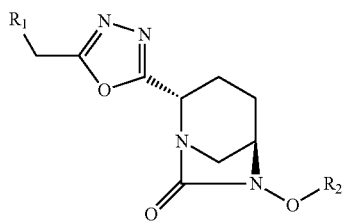

Formula (I)

or a stereoisomer or a pharmaceutically acceptable derivative thereof;

wherein

R$_1$ is as defined earlier elsewhere in the text;

R$_2$ is —SO$_3$M;

said process comprising:

(a) reacting a compound of Formula (Ia) with R$_1$CONHNH$_2$ (Ib) in presence of coupling agent to obtain a compound of Formula (Ic);

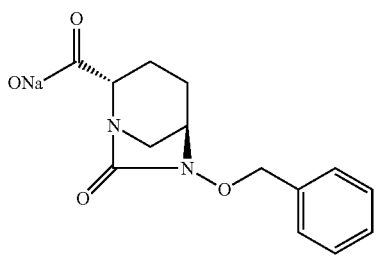

(Ia)

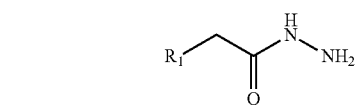

(Ib)

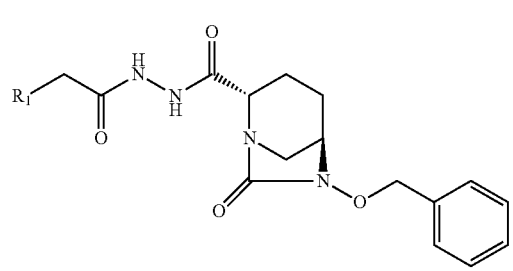

(Ic)

(b) cyclizing a compound of Formula (Ic) to obtain a compound of Formula (Id);

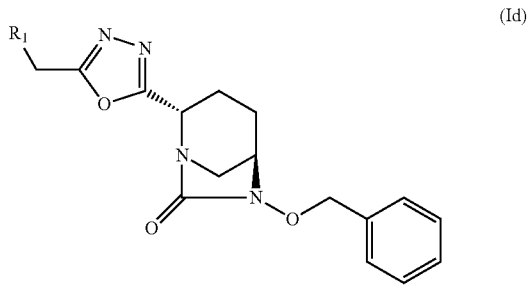

(Id)

(c) hydrogenolysis of a compound of Formula (Id) to obtain a compound of Formula (Ie);

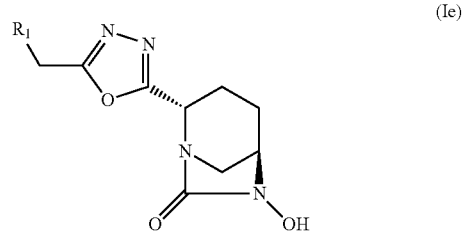

(Ie)

(d) sulfonating a compound of Formula (Ie), followed by the treatment with tetrabutyl ammonium hydrogen sulfate to obtain a compound of Formula (If); and

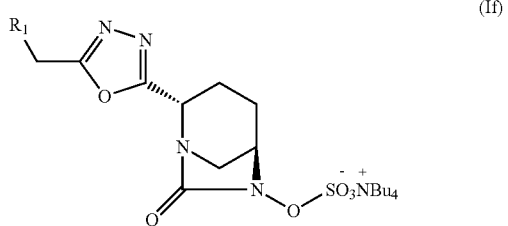

(If)

(e) converting a compound of Formula (If) to obtain a compound of Formula (I).

In general, the compounds of Formula (I), wherein R$_2$ is —SO$_3$M, are prepared as described in Scheme-1. Typically, sodium salt of 6-benzyloxy-7-oxo-1,6-diaza-bicyclo[3.2.1] octane-2-carboxylic acid (Ia), is reacted with suitable acid hydrazides (Ib) in presence of a suitable coupling agent such as EDC hydrochloride, HOBt, dicyclohexylcarodiimide (DCC), pivalyl chloride and the like, in suitable solvent such as water, N,N-dimethylformamide, N,N-dimethylacetamide, or 1,4-dioxane, at a temperature ranging from about −15° C. to 60° C. for about 1 hour to 24 hours to obtain a compound of Formula (Ic). In some embodiments, compound of Formula (Ia) is reacted with a compound of Formula (Ib) in presence of EDC hydrochloride and HOBt at a temperature of about 25° C. for about 1 hour to 24 hours to obtain a compound of Formula (Ic).

The compound of Formula (Ic) is cyclized by treating it with a suitable reagent such as p-toluenesulfonyl chloride, p-nitrobenzenesulfonyl chloride or methanesulfonyl chloride, in a suitable solvent such as toluene, chloroform, dichloromethane, or N, N-dimethylformamide, at a temperature ranging from about 25° C. to about 110° C., for about 1 hour to 14 hours to provide 1,3,4-oxadiazol-2-yl compound of Formula (Id). In some embodiments, cyclization of a compound of Formula (Ic) was carried by treating with p-toluenesulfonyl chloride, in presence of N,N-dimethylformamide at a temperature ranging from about 55° to about 100° C. for about 1 hour to 14 hours to provide 1,3,4-oxadiazol-2-yl compound of Formula (Id).

The compound of Formula (Id) is subjected to hydrogenolysis in presence of a suitable catalyst such as 5% or 10% palladium on carbon, 20% palladium hydroxide on carbon, in presence of suitable hydrogen source such as hydrogen gas, ammonium formate, or cyclohexene, in presence of a suitable solvent such as methanol, ethanol, methanol-dichloromethane mixture, or N,N-dimethylformamide-dichloromethane mixture, at a temperature ranging from about 25° C. to 60° C. for about 1 to 14 hours to obtain a compound of Formula (Ie). In some embodiments, compound of Formula (Id) is converted to a compound of Formula (Ie) in presence of 10% palladium on carbon and hydrogen at a temperature of about 25° C. for about 1 hour to about 14 hours.

The compound of Formula (Ie) is sulfonated by reacting with a suitable sulfonating reagent such as sulfur trioxide-pyridine complex, or sulfur trioxide-N,N-dimethylformamide complex, in presence of a suitable solvent such as pyridine, or N,N-dimethyl formamide, at a temperature ranging from about 25° C. to 90° C. for about 1 hour to about 24 hours to obtain corresponding pyridine salt of sulfonic acid. This is further treated with suitable reagent such as tetrabutylammonium acetate, tetrabutylammonium hydrogen sulfate, tetrabutylammonium sulfate and the like to provide tetrabutylammonium salt of sulfonic acid as a compound of Formula (If). In some embodiments, compound of Formula (Ie) is sulfonated in presence of sulfur trioxide-pyridine complex at a temperature of about 25° C. for about 1 hour to about 24 hours. The sulphonated compound is further treated with tetrabutylammonium hydrogen sulfate to provide a compound of Formula (If).

Some compounds according to invention are isolated as zwitterions, by treating a compound of Formula (If) with trifluoroacetic acid, in a suitable solvent such as dichloromethane, chloroform, or acetonitrile, at a temperature ranging from about −15° C. to 40° C. for about 0.5 to 14 hours. In some embodiments, compound of Formula (If) is treated with trifluoroacetic acid in presence of dichloromethane at a temperature of about −10° C. for about 2 hours to obtain a compound of Formula (I), wherein $R_2$ is —$SO_3M$.

Some other compounds according to the invention are isolated as a corresponding sodium salt, by passing intermediate compound of Formula (If) through sodium form of Amberlite 200C resin in a tetrahydrofuran-water mixture followed by evaporation of the solvent under vacuum.

Scheme-1

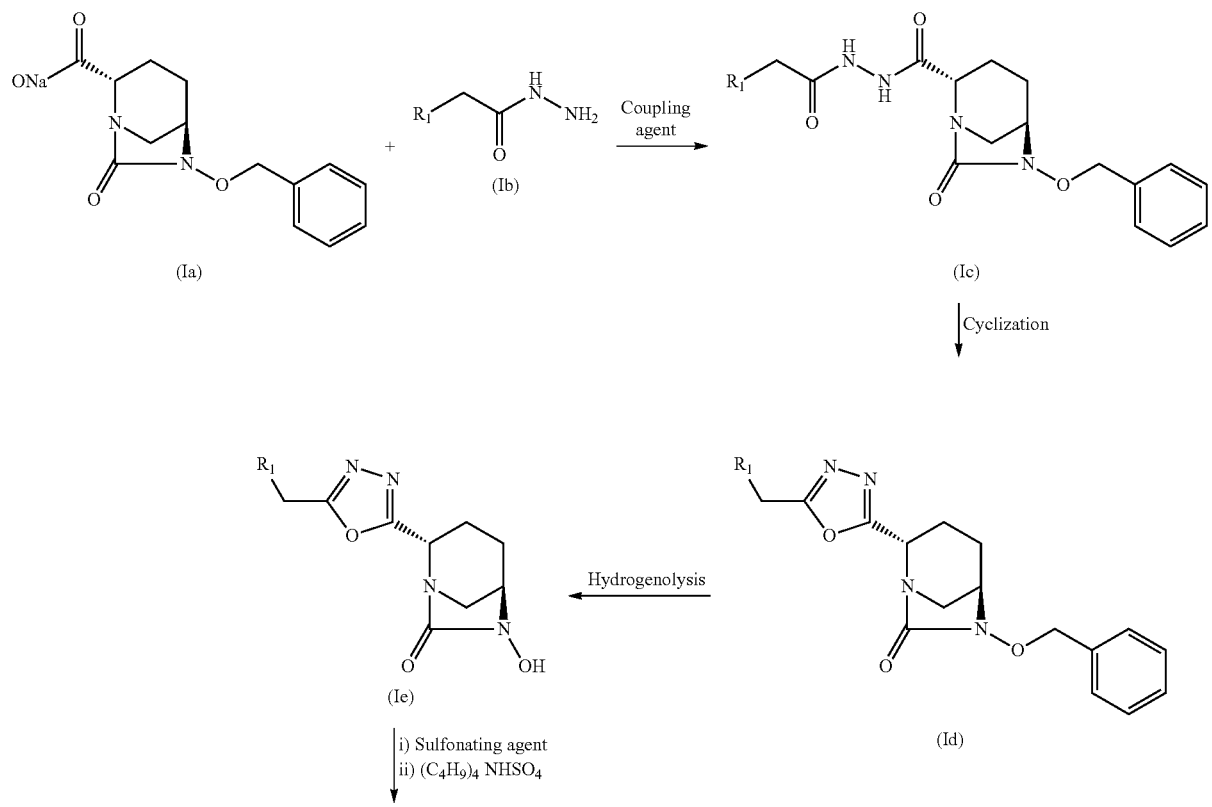

-continued

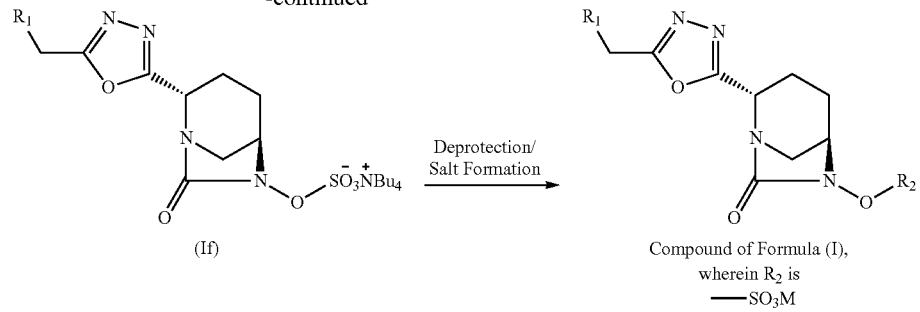

(If) → Deprotection/Salt Formation → Compound of Formula (I), wherein R₂ is —SO₃M The compounds according to invention wherein $R_2$ is selected from $CF_2COOM$ or $CHFCOOM$ or $CH_2COOM$ are prepared by general reaction scheme as described in Scheme-2. The hydroxyl intermediate (Ie) obtained as per Scheme-1, is subjected to alkylation with an alkylating agent (IIa) such as ethyl-bromoacetate, ethyl-bromofluoroacetate, or ethyl-bromodifluoroacetate, in presence of a base such as potassium carbonate, diisopropylethylamine or triethylamine, in a suitable solvent such as N,N-dimethyl formamide, N,N-dimethylacetamide or N-methyl pyrrolidine, to provide O-alkylated compound (IIb).

The compound of Formula (IIb) is subjected for hydrolysis in presence of a base such as lithium hydroxide or potassium hydroxide, in a suitable solvent such as aqueous tetrahydrofuran or aqueous dioxane, to provide compound of Formula (I). Optionally, if $R_1$ bears amine function protected with Boc group, then it is removed with an additional step of deprotection by using a suitable deprotecting agent (such as trifluoroacetic acid or hydrogen fluoride-pyridine) in a suitable solvent such as dichloromethane, chloroform or acetonitrile, to provide a compound of Formula (I), wherein, $R_2$ is selected from $CF_2COOM$ or $CHFCOOM$ or $CH_2COOM$.

Scheme-2

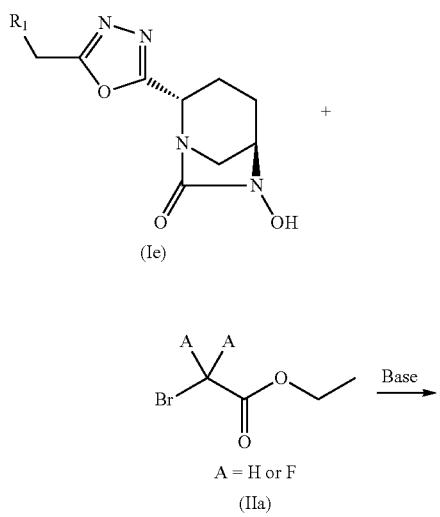

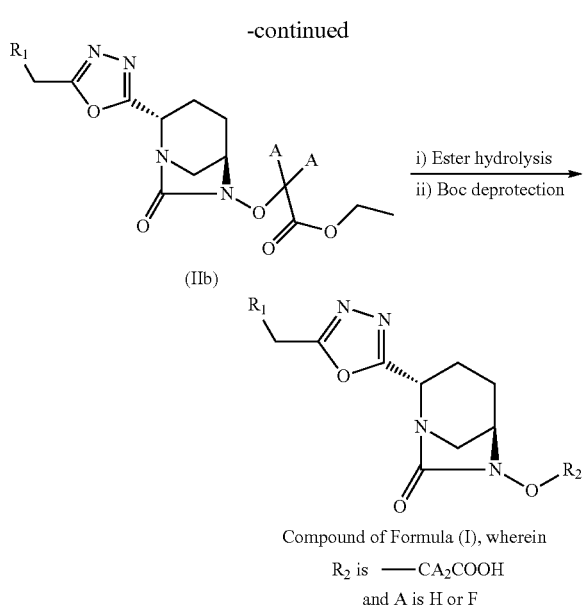

(IIb) → i) Ester hydrolysis ii) Boc deprotection →

Compound of Formula (I), wherein
$R_2$ is —CA₂COOH
and A is H or F

In some embodiments, there are provided pharmaceutical compositions comprising a compound of Formula (I) or a stereoisomer or a pharmaceutically acceptable derivative thereof.

In some other embodiments, there are provided pharmaceutical compositions comprising: (a) a compound of Formula (I) or a stereoisomer or a pharmaceutically acceptable derivative thereof, and (b) at least one beta-lactamase inhibitor or a pharmaceutically acceptable derivative thereof.

In some other embodiments, there are provided pharmaceutical compositions comprising: (a) a compound of Formula (I) or a stereoisomer or a pharmaceutically acceptable derivative thereof, and (b) at least one beta-lactamase inhibitor selected from sulbactam, tazobactam, clavulanic acid, avibactam or a pharmaceutically acceptable derivative thereof.

In some other embodiments, there are provided pharmaceutical compositions comprising: (a) a compound of Formula (I) or a stereoisomer or a pharmaceutically acceptable derivative thereof, and (b) at least one antibacterial agent or a pharmaceutically acceptable derivative thereof.

In some other embodiments, there are provided pharmaceutical compositions comprising: (a) a compound of Formula (I) or a stereoisomer or a pharmaceutically acceptable derivative thereof, and (b) at least one antibacterial agent selected from cefepime, cefpirome, ceftaroline, ceftazidime, ceftalozane or a pharmaceutically acceptable derivative thereof.

In some other embodiments, there are provided pharmaceutical compositions comprising: (a) a compound of Formula (I) or a stereoisomer or a pharmaceutically acceptable derivative thereof, (b) at least one beta-lacatamse inhibitor or a pharmaceutically acceptable derivative thereof, and (c) at least one antibacterial agent, or a pharmaceutically acceptable derivative thereof.

In some other embodiments, there are provided methods for preventing or treating a bacterial infection in a subject, said methods comprising administering to said subject a pharmaceutical composition comprising a compound of Formula (I) or a stereoisomer or a pharmaceutically acceptable derivative thereof.

In some other embodiments, there are provided methods for preventing or treating a bacterial infection in a subject, said methods comprising administering to said subject a pharmaceutical composition comprising: (a) a compound of Formula (I), or a stereoisomer or a pharmaceutically acceptable derivative thereof and (b) at least one beta-lactamase inhibitor or pharmaceutically acceptable derivative thereof.

In some other embodiments, there are provided methods for preventing or treating a bacterial infection in a subject, said methods comprising administering to said subject a pharmaceutical composition comprising: (a) a compound of Formula (I), or a stereoisomer or a pharmaceutically acceptable derivative thereof and (b) at least one beta-lactamase inhibitor selected from sulbactam, tazobactam, clavulanic acid, avibactam, or pharmaceutically acceptable derivative thereof.

In some other embodiments, there are provided methods for preventing or treating a bacterial infection in a subject, said methods comprising administering to said subject a pharmaceutical composition comprising: (a) a compound of Formula (I) or a stereoisomer or a pharmaceutically acceptable derivative thereof, and (b) at least one antibacterial agent or a pharmaceutically acceptable derivative thereof.

In some other embodiments, there are provided methods for preventing or treating a bacterial infection in a subject, said methods comprising administering to said subject a pharmaceutical composition comprising: (a) a compound of Formula (I) or a stereoisomer or a pharmaceutically acceptable derivative thereof, and (b) at least one antibacterial agent selected from selected from cefepime, cefpirome, ceftaroline, ceftazidime, ceftalozane or a pharmaceutically acceptable derivative thereof.

In some other embodiments, there are provided methods for preventing or treating a bacterial infection in a subject, said methods comprising administering to said subject a pharmaceutical composition comprising: (a) a compound of Formula (I) or a stereoisomer or a pharmaceutically acceptable derivative thereof, (b) at least one beta-lactamase inhibitor or pharmaceutically acceptable derivative thereof and (c) at least one antibacterial agent or a pharmaceutically acceptable derivative thereof.

In some other embodiments, there are provided methods for preventing or treating a bacterial infection in a subject, said method comprising administering to said subject a compound of Formula (I) or a stereoisomer or a pharmaceutically acceptable derivative thereof.

In some other embodiments, there are provided methods for preventing or treating a bacterial infection in a subject, said methods comprising administering to said subject: (a) a compound of Formula (I) or a stereoisomer or a pharmaceutically acceptable derivative thereof, (b) at least one beta-lactamase inhibitor or pharmaceutically acceptable derivative thereof.

In some other embodiments, there are provided methods for preventing or treating a bacterial infection in a subject, said methods comprising administering to said subject: (a) a compound of Formula (I) or a stereoisomer or a pharmaceutically acceptable derivative thereof, (b) at least one beta-lactamase inhibitor selected from sulbactam, tazobactam, clavulanic acid, avibactam, or pharmaceutically acceptable derivative thereof.

In some other embodiments, there are provided methods for preventing or treating a bacterial infection in a subject, said methods comprising administering to said subject: (a) a compound of Formula (I) or a stereoisomer or a pharmaceutically acceptable derivative thereof, (b) at least one antibacterial agent or pharmaceutically acceptable derivative thereof.

In some other embodiments, there are provided methods for preventing or treating a bacterial infection in a subject, said methods comprising administering to said subject: (a) a compound of Formula (I) or a stereoisomer or a pharmaceutically acceptable derivative thereof, (b) at least one antibacterial agent selected from selected from cefepime, cefpirome, ceftaroline, ceftazidime, ceftalozane or pharmaceutically acceptable derivative thereof.

In some other embodiments, there are provided methods for preventing or treating a bacterial infection in a subject, said methods comprising administering to said subject: (a) a compound of Formula (I) or a stereoisomer or a pharmaceutically acceptable derivative thereof, (b) at least one beta-lactamase inhibitor or pharmaceutically acceptable derivative thereof, and (c) at least one antibacterial agent or pharmaceutically acceptable derivative thereof.

In some embodiments, there are provided pharmaceutical compositions comprising (2S,5R)-sulfuric acid mono-[2-(5-benzhydryl-[1,3,4]-oxadiazol-2-yl)-7-oxo-1,6-diaza-bicyclo [3.2.1] oct-6-yl] ester or a stereoisomer or a pharmaceutically acceptable derivative thereof.

In some other embodiments, there are provided pharmaceutical compositions comprising: (a) (2S,5R)-sulfuric acid mono-[2-(5-benzhydryl-[1,3,4]-oxadiazol-2-yl)-7-oxo-1,6-diaza-bicyclo[3.2.1] oct-6-yl] ester or a stereoisomer or a pharmaceutically acceptable derivative thereof, and (b) at least one beta-lactamase inhibitor or a pharmaceutically acceptable derivative thereof.

In some other embodiments, there are provided pharmaceutical compositions comprising: (a) (2S,5R)-sulfuric acid mono-[2-(5-benzhydryl-[1,3,4]-oxadiazol-2-yl)-7-oxo-1,6-diaza-bicyclo[3.2.1] oct-6-yl] ester or a stereoisomer or a pharmaceutically acceptable derivative thereof, and (b) at least one beta-lactamase inhibitor selected from sulbactam, tazobactam, clavulanic acid, avibactam or a pharmaceutically acceptable derivative thereof.

In some other embodiments, there are provided pharmaceutical compositions comprising: (a) (2S,5R)-sulfuric acid mono-[2-(5-benzhydryl-[1,3,4]-oxadiazol-2-yl)-7-oxo-1,6-diaza-bicyclo[3.2.1] oct-6-yl] ester or a stereoisomer or a pharmaceutically acceptable derivative thereof, and (b) at least one antibacterial agent or a pharmaceutically acceptable derivative thereof.

In some other embodiments, there are provided pharmaceutical compositions comprising: (a) (2S,5R)-sulfuric acid mono-[2-(5-benzhydryl-[1,3,4]-oxadiazol-2-yl)-7-oxo-1,6-diaza-bicyclo[3.2.1] oct-6-yl] ester or a stereoisomer or a pharmaceutically acceptable derivative thereof, and (b) at least one antibacterial agent selected from cefepime, cefpirome, ceftaroline, ceftazidime, ceftalozane or a pharmaceutically acceptable derivative thereof.

In some other embodiments, there are provided pharmaceutical compositions comprising: (a) (2S,5R)-sulfuric acid mono-[2-(5-benzhydryl-[1,3,4]-oxadiazol-2-yl)-7-oxo-1,6-diaza-bicyclo[3.2.1] oct-6-yl] ester or a pharmaceutically acceptable derivative thereof, (b) at least one beta-lacatamse inhibitor or a pharmaceutically acceptable derivative thereof, and (c) at least one antibacterial agent, or a pharmaceutically acceptable derivative thereof.

In some other embodiments, there are provided methods for preventing or treating a bacterial infection in a subject, said methods comprising administering to said subject a pharmaceutical composition comprising (2S,5R)-sulfuric acid mono-[2-(5-benzhydryl-[1,3,4]-oxadiazol-2-yl)-7-oxo-1,6-diaza-bicyclo[3.2.1] oct-6-yl] ester or a stereoisomer or a pharmaceutically acceptable derivative thereof.

In some other embodiments, there are provided methods for preventing or treating a bacterial infection in a subject, said methods comprising administering to said subject a pharmaceutical composition comprising: (a) (2S,5R)-sulfuric acid mono-[2-(5-benzhydryl-[1,3,4]-oxadiazol-2-yl)-7-oxo-1,6-diaza-bicyclo[3.2.1] oct-6-yl] ester or a stereoisomer or a pharmaceutically acceptable derivative thereof and (b) at least one beta-lactamase inhibitor or pharmaceutically acceptable derivative thereof.

In some other embodiments, there are provided methods for preventing or treating a bacterial infection in a subject, said methods comprising administering to said subject a pharmaceutical composition comprising: (a) (2S,5R)-sulfuric acid mono-[2-(5-benzhydryl-[1,3,4]-oxadiazol-2-yl)-7-oxo-1,6-diaza-bicyclo[3.2.1] oct-6-yl] ester or a stereoisomer or a pharmaceutically acceptable derivative thereof and (b) at least one beta-lactamase inhibitor selected from sulbactam, tazobactam, clavulanic acid, avibactam, or pharmaceutically acceptable derivative thereof.

In some other embodiments, there are provided methods for preventing or treating a bacterial infection in a subject, said methods comprising administering to said subject a pharmaceutical composition comprising: (a) (2S,5R)-sulfuric acid mono-[2-(5-benzhydryl-[1,3,4]-oxadiazol-2-yl)-7-oxo-1,6-diaza-bicyclo[3.2.1] oct-6-yl] ester or a stereoisomer or a pharmaceutically acceptable derivative thereof, and (b) at least one antibacterial agent or a pharmaceutically acceptable derivative thereof.

In some other embodiments, there are provided methods for preventing or treating a bacterial infection in a subject, said methods comprising administering to said subject a pharmaceutical composition comprising: (a) (2S,5R)-sulfuric acid mono-[2-(5-benzhydryl-[1,3,4]-oxadiazol-2-yl)-7-oxo-1,6-diaza-bicyclo[3.2.1] oct-6-yl] ester or a stereoisomer or a pharmaceutically acceptable derivative thereof, and (b) at least one antibacterial agent selected from selected from cefepime, cefpirome, ceftaroline, ceftazidime, ceftalozane or a pharmaceutically acceptable derivative thereof.

In some other embodiments, there are provided methods for preventing or treating a bacterial infection in a subject, said methods comprising administering to said subject a pharmaceutical composition comprising: (a) (2S,5R)-sulfuric acid mono-[2-(5-benzhydryl-[1,3,4]-oxadiazol-2-yl)-7-oxo-1,6-diaza-bicyclo[3.2.1] oct-6-yl] ester or a stereoisomer or a pharmaceutically acceptable derivative thereof, (b) at least one beta-lactamase inhibitor or pharmaceutically acceptable derivative thereof and (c) at least one antibacterial agent or a pharmaceutically acceptable derivative thereof.

In some other embodiments, there are provided methods for preventing or treating a bacterial infection in a subject, said method comprising administering to said subject (2S, 5R)-sulfuric acid mono-[2-(5-benzhydryl-[1,3,4]-oxadiazol-2-yl)-7-oxo-1,6-diaza-bicyclo[3.2.1] oct-6-yl] ester or a stereoisomer or a pharmaceutically acceptable derivative thereof.

In some other embodiments, there are provided methods for preventing or treating a bacterial infection in a subject, said methods comprising administering to said subject: (a) (2S,5R)-sulfuric acid mono-[2-(5-benzhydryl-[1,3,4]-oxadiazol-2-yl)-7-oxo-1,6-diaza-bicyclo[3.2.1] oct-6-yl] ester or a stereoisomer or a pharmaceutically acceptable derivative thereof, (b) at least one beta-lactamase inhibitor or pharmaceutically acceptable derivative thereof.

In some other embodiments, there are provided methods for preventing or treating a bacterial infection in a subject, said methods comprising administering to said subject: (a) (2S,5R)-sulfuric acid mono-[2-(5-benzhydryl-[1,3,4]-oxadiazol-2-yl)-7-oxo-1,6-diaza-bicyclo[3.2.1] oct-6-yl] ester or a stereoisomer or a pharmaceutically acceptable derivative thereof, (b) at least one beta-lactamase inhibitor selected from sulbactam, tazobactam, clavulanic acid, avibactam, or pharmaceutically acceptable derivative thereof.

In some other embodiments, there are provided methods for preventing or treating a bacterial infection in a subject, said methods comprising administering to said subject: (a) (2S,5R)-sulfuric acid mono-[2-(5-benzhydryl-[1,3,4]-oxadiazol-2-yl)-7-oxo-1,6-diaza-bicyclo[3.2.1] oct-6-yl] ester or a stereoisomer or a pharmaceutically acceptable derivative thereof, (b) at least one antibacterial agent or pharmaceutically acceptable derivative thereof.

In some other embodiments, there are provided methods for preventing or treating a bacterial infection in a subject, said methods comprising administering to said subject: (a) (2S,5R)-sulfuric acid mono-[2-(5-benzhydryl-[1,3,4]-oxadiazol-2-yl)-7-oxo-1,6-diaza-bicyclo[3.2.1] oct-6-yl] ester or a stereoisomer or a pharmaceutically acceptable derivative thereof, (b) at least one antibacterial agent selected from selected from cefepime, cefpirome, ceftaroline, ceftazidime, ceftalozane or pharmaceutically acceptable derivative thereof.

In some other embodiments, there are provided methods for preventing or treating a bacterial infection in a subject, said methods comprising administering to said subject: (a) (2S,5R)-sulfuric acid mono-[2-(5-benzhydryl-[1,3,4]-oxadiazol-2-yl)-7-oxo-1,6-diaza-bicyclo[3.2.1] oct-6-yl] ester or a stereoisomer or a pharmaceutically acceptable derivative thereof, (b) at least one beta-lactamase inhibitor or pharmaceutically acceptable derivative thereof, and (c) at least one antibacterial agent or pharmaceutically acceptable derivative thereof.

In some embodiments, there are provided pharmaceutical compositions comprising (2S,5R)-sulfuric acid mono-[2-(5-(4-hydroxybenzyl)-[1,3,4]-oxadiazol-2-yl)-7-oxo-1,6-diaza-bicyclo[3.2.1] oct-6-yl] ester or a stereoisomer or a pharmaceutically acceptable derivative thereof.

In some other embodiments, there are provided pharmaceutical compositions comprising: (a) (2S,5R)-sulfuric acid mono-[2-(5-(4-hydroxybenzyl)-[1,3,4]-oxadiazol-2-yl)-7-oxo-1,6-diaza-bicyclo[3.2.1] oct-6-yl] ester or a stereoisomer or a pharmaceutically acceptable derivative thereof, and (b) at least one beta-lactamase inhibitor or a pharmaceutically acceptable derivative thereof.

In some other embodiments, there are provided pharmaceutical compositions comprising: (a) (2S,5R)-sulfuric acid mono-[2-(5-(4-hydroxybenzyl)-[1,3,4]-oxadiazol-2-yl)-7-oxo-1,6-diaza-bicyclo[3.2.1] oct-6-yl] ester or a stereoisomer or a pharmaceutically acceptable derivative thereof, and (b) at least one beta-lactamase inhibitor selected from sulbactam, tazobactam, clavulanic acid, avibactam or a pharmaceutically acceptable derivative thereof.

In some other embodiments, there are provided pharmaceutical compositions comprising: (a) (2S,5R)-sulfuric acid mono-[2-(5-(4-hydroxybenzyl)-[1,3,4]-oxadiazol-2-yl)-7-oxo-1,6-diaza-bicyclo[3.2.1] oct-6-yl] ester or a stereoisomer or a pharmaceutically acceptable derivative thereof, and (b) at least one antibacterial agent or a pharmaceutically acceptable derivative thereof.

In some other embodiments, there are provided pharmaceutical compositions comprising: (a) (2S,5R)-sulfuric acid mono-[2-(5-(4-hydroxybenzyl)-[1,3,4]-oxadiazol-2-yl)-7-oxo-1,6-diaza-bicyclo[3.2.1] oct-6-yl] ester or a stereoisomer or a pharmaceutically acceptable derivative thereof, and (b) at least one antibacterial agent selected from cefepime, cefpirome, ceftaroline, ceftazidime, ceftalozane or a pharmaceutically acceptable derivative thereof.

In some other embodiments, there are provided pharmaceutical compositions comprising: (a) (2S,5R)-sulfuric acid mono-[2-(5-(4-hydroxybenzyl)-[1,3,4]-oxadiazol-2-yl)-7-oxo-1,6-diaza-bicyclo[3.2.1] oct-6-yl] ester or a stereoisomer or a pharmaceutically acceptable derivative thereof, (b) at least one beta-lacatamse inhibitor or a pharmaceutically acceptable derivative thereof, and (c) at least one antibacterial agent, or a pharmaceutically acceptable derivative thereof.

In some other embodiments, there are provided methods for preventing or treating a bacterial infection in a subject, said methods comprising administering to said subject a pharmaceutical composition comprising (2S,5R)-sulfuric acid mono-[2-(5-(4-hydroxybenzyl)-[1,3,4]-oxadiazol-2-yl)-7-oxo-1,6-diaza-bicyclo[3.2.1] oct-6-yl] ester or a stereoisomer or a pharmaceutically acceptable derivative thereof.

In some other embodiments, there are provided methods for preventing or treating a bacterial infection in a subject, said methods comprising administering to said subject a pharmaceutical composition comprising: (a) (2S,5R)-sulfuric acid mono-[2-(5-(4-hydroxybenzyl)-[1,3,4]-oxadiazol-2-yl)-7-oxo-1,6-diaza-bicyclo[3.2.1] oct-6-yl] ester or a stereoisomer or a pharmaceutically acceptable derivative thereof and (b) at least one beta-lactamase inhibitor or pharmaceutically acceptable derivative thereof.

In some other embodiments, there are provided methods for preventing or treating a bacterial infection in a subject, said methods comprising administering to said subject a pharmaceutical composition comprising: (a) (2S,5R)-sulfuric acid mono-[2-(5-(4-hydroxybenzyl)-[1,3,4]-oxadiazol-2-yl)-7-oxo-1,6-diaza-bicyclo[3.2.1] oct-6-yl] ester or a stereoisomer or a pharmaceutically acceptable derivative thereof and (b) at least one beta-lactamase inhibitor selected from sulbactam, tazobactam, clavulanic acid, avibactam, or pharmaceutically acceptable derivative thereof.

In some other embodiments, there are provided methods for preventing or treating a bacterial infection in a subject, said methods comprising administering to said subject a pharmaceutical composition comprising: (a) (2S,5R)-sulfuric acid mono-[2-(5-(4-hydroxybenzyl)-[1,3,4]-oxadiazol-2-yl)-7-oxo-1,6-diaza-bicyclo[3.2.1] oct-6-yl] ester or a stereoisomer or a pharmaceutically acceptable derivative thereof, and (b) at least one antibacterial agent or a pharmaceutically acceptable derivative thereof.

In some other embodiments, there are provided methods for preventing or treating a bacterial infection in a subject, said methods comprising administering to said subject a pharmaceutical composition comprising: (a) (2S,5R)-sulfuric acid mono-[2-(5-(4-hydroxybenzyl)-[1,3,4]-oxadiazol-2-yl)-7-oxo-1,6-diaza-bicyclo[3.2.1] oct-6-yl] ester or a stereoisomer or a pharmaceutically acceptable derivative thereof, and (b) at least one antibacterial agent selected from cefepime, cefpirome, ceftaroline, ceftazidime, ceftalozane or a pharmaceutically acceptable derivative thereof.

In some other embodiments, there are provided methods for preventing or treating a bacterial infection in a subject, said methods comprising administering to said subject a pharmaceutical composition comprising: (a) (2S,5R)-sulfuric acid mono-[2-(5-(4-hydroxybenzyl)-[1,3,4]-oxadiazol-2-yl)-7-oxo-1,6-diaza-bicyclo[3.2.1] oct-6-yl] ester or a stereoisomer or a pharmaceutically acceptable derivative thereof, (b) at least one beta-lactamase inhibitor or pharmaceutically acceptable derivative thereof and (c) at least one antibacterial agent or a pharmaceutically acceptable derivative thereof.

In some other embodiments, there are provided methods for preventing or treating a bacterial infection in a subject, said method comprising administering to said subject (2S,5R)-sulfuric acid mono-[2-(5-(4-hydroxybenzyl)-[1,3,4]-oxadiazol-2-yl)-7-oxo-1,6-diaza-bicyclo[3.2.1] oct-6-yl] ester or a stereoisomer or a pharmaceutically acceptable derivative thereof.

In some other embodiments, there are provided methods for preventing or treating a bacterial infection in a subject, said methods comprising administering to said subject: (a) (2S,5R)-sulfuric acid mono-[2-(5-(4-hydroxybenzyl)-[1,3,4]-oxadiazol-2-yl)-7-oxo-1,6-diaza-bicyclo[3.2.1] oct-6-yl] ester or a stereoisomer or a pharmaceutically acceptable derivative thereof, (b) at least one beta-lactamase inhibitor or pharmaceutically acceptable derivative thereof.

In some other embodiments, there are provided methods for preventing or treating a bacterial infection in a subject, said methods comprising administering to said subject: (a) (2S,5R)-sulfuric acid mono-[2-(5-(4-hydroxybenzyl)-[1,3,4]-oxadiazol-2-yl)-7-oxo-1,6-diaza-bicyclo[3.2.1] oct-6-yl] ester or a stereoisomer or a pharmaceutically acceptable derivative thereof, (b) at least one beta-lactamase inhibitor selected from sulbactam, tazobactam, clavulanic acid, avibactam, or pharmaceutically acceptable derivative thereof.

In some other embodiments, there are provided methods for preventing or treating a bacterial infection in a subject, said methods comprising administering to said subject: (a) (2S,5R)-sulfuric acid mono-[2-(5-(4-hydroxybenzyl)-[1,3,4]-oxadiazol-2-yl)-7-oxo-1,6-diaza-bicyclo[3.2.1] oct-6-yl] ester or a stereoisomer or a pharmaceutically acceptable derivative thereof, (b) at least one antibacterial agent or pharmaceutically acceptable derivative thereof.

In some other embodiments, there are provided methods for preventing or treating a bacterial infection in a subject, said methods comprising administering to said subject: (a) (2S,5R)-sulfuric acid mono-[2-(5-(4-hydroxybenzyl)-[1,3,4]-oxadiazol-2-yl)-7-oxo-1,6-diaza-bicyclo[3.2.1] oct-6-yl] ester or a stereoisomer or a pharmaceutically acceptable derivative thereof, (b) at least one antibacterial agent selected from selected from cefepime, cefpirome, ceftaroline, ceftazidime, ceftalozane or pharmaceutically acceptable derivative thereof.

In some other embodiments, there are provided methods for preventing or treating a bacterial infection in a subject, said methods comprising administering to said subject: (a) (2S,5R)-sulfuric acid mono-[2-(5-(4-hydroxybenzyl)-[1,3,4]-oxadiazol-2-yl)-7-oxo-1,6-diaza-bicyclo[3.2.1] oct-6-yl] ester or a stereoisomer or a pharmaceutically acceptable derivative thereof, (b) at least one beta-lactamase inhibitor or pharmaceutically acceptable derivative thereof, and (c) at least one antibacterial agent or pharmaceutically acceptable derivative thereof.

In some embodiments, the compositions and methods according to the invention use compounds of Formula (I), or a stereoisomer, or a pharmaceutically acceptable derivative thereof, in combination with at least one antibacterial agent. A wide variety of antibacterial agents can be used. Typical, non-limiting examples of antibacterial agents include one or more of antibacterial compounds generally classified as aminoglycosides, ansamycins, carbacephems, cephalosporins, cephamycins, lincosamides, lipopeptides, macrolides, monobactams, nitrofurans, penicillins, polypeptides, quinolones, sulfonamides, tetracyclines, oxazolidinone and the like. Typical, non-limiting examples of aminoglycoside antibacterial agents include amikacin, gentamicin, kanamycin, neomycin, netilmicin, tobramycin, paromomycin, arbekacin, streptomycin, apramycin and the like. Typical, non-limiting examples of ansamycin antibacterial agents include geldanamycin, herbimycin and the like. Typical, non-limiting examples of carbacephem antibacterial agents include loracarbef and the like. Typical, non-limiting examples of carbapenam antibacterial agents include ertapenem, doripenem, imipenem, meropenem and the like.

Typical, non-limiting examples of cephalosporin and cephamycin antibacterial agents include cefazolin, cefacetrile, cefadroxil, cefalexin, cefaloglycin, cefalonium, cefaloridine, cefalotin, cefapirin, cefatrizine, cefazedone, cefazaflur, cefradine, cefroxadine, ceftezole, cefaclor, cefamandole, cefminox, cefonicid, ceforanide, cefotiam, cefprozil, cefbuperazone, cefuroxime, cefuzonam, cephamycin, cefoxitin, cefotetan, cefmetazole, carbacephem, cefixime, ceftazidime, ceftriaxone, cefcapene, cefdaloxime, cefdinir, cefditoren, cefetamet, cefmenoxime, cefodizime, cefoperazone, cefotaxime, cefpimizole, cefpiramide, cefpodoxime, cefsulodin, cefteram, ceftibuten, cefiolene, ceftizoxime, oxacephem, cefepime, cefozopran, cefpirome, cefquinome, ceftobiprole, cetiofur, cefquinome, cefovecin, CXA-101, ceftaroline, ceftobiprole, cefoselis, cefluprenam, cefclidin, loracarbacef, ceftolozane, latamoxef and the like.

Typical, non-limiting examples of lincosamide antibacterial agents include clindamycin, lincomycin and the like. Typical, non-limiting examples of macrolide antibacterial agents include azithromycin, clarithromycin, dirithromycin, erythromycin, roxithromycin, troleandomycin, telithromycin, spectinomycin and the like. Typical, non-limiting examples of monobactam antibacterial agents include aztreonam and the like. Typical, non-limiting examples of nitrofuran antibacterial agents include furazolidone, nitrofurantoin and the like. Typical, non-limiting examples of penicillin antibacterial agents include amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, colistin, polymyxin B and the like.

Typical, non-limiting examples of polypeptide antibacterial agents include bacitracin, colistin, polymyxin B and the like. Typical, non-limiting examples of quinolone antibacterial agents include ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin and the like. Typical, non-limiting examples of sulfonamide antibacterial agents include mafenide, sulfonamidochrysoidine, sulfacetamide, sulfadiazine, sulfamethizole, sulfamethoxazole, sulfasalazine, sulfisoxazole, trimethoprim and the like. Typical, non-limiting examples of tetracycline antibacterial agents include demeclocycline, doxycycline, minocycline, oxytetracycline, tetracycline, tigecycline and the like. Typical non-limiting examples of oxazolidinone anti-bacterial agents include linezolid, ranbezolid, torezolid, radezolid and the like. Typical non-limiting examples of beta-lactamase inhibitor include sulbactam, tazobactam, clavulanic acid, avibactam and the like.

The pharmaceutical compositions according to the invention may include one or more pharmaceutically acceptable carriers or excipients or the like. Typical, non-limiting examples of such carriers or excipients include mannitol, lactose, starch, magnesium stearate, sodium saccharine, talcum, cellulose, sodium crosscarmellose, glucose, gelatin, sucrose, magnesium carbonate, wetting agents, emulsifying agents, solubilizing agents, pH buffering agents, lubricants, preservatives, stabilizing agents, binding agents etc.

The pharmaceutical compositions according to this invention can exist in various forms. In some embodiments, the pharmaceutical composition is in the form of a powder or a solution. In some other embodiments, the pharmaceutical compositions according to the invention are in the form of a powder that can be reconstituted by addition of a compatible reconstitution diluent prior to parenteral administration. Non-limiting example of such a compatible reconstitution diluent includes water.

In some other embodiments, the pharmaceutical compositions according to the invention are in the form of a frozen composition that can be diluted with a compatible diluent prior to parenteral administration.

In some other embodiments, the pharmaceutical compositions according to the invention are in the form ready to use for oral or parenteral administration.

In the methods according to the invention, the pharmaceutical composition and/or other pharmaceutically active ingredients disclosed herein may be administered by any appropriate method, which serves to deliver the composition or its constituents or the active ingredients to the desired site. The method of administration can vary depending on various factors, such as for example, the components of the pharmaceutical composition and the nature of the active ingredients, the site of the potential or actual infection, the microorganism (e.g. bacteria) involved, severity of infection, age and physical condition of the subject. Some non-limiting examples of administering the composition to a subject according to this invention include oral, intravenous, topical, intrarespiratory, intraperitoneal, intramuscular, parenteral, sublingual, transdermal, intranasal, aerosol, intraocular, intratracheal, intrarectal, vaginal, gene gun, dermal patch, eye drop, ear drop or mouthwash. In some embodiments, compounds and compositions according to invention are administered orally or parenterally.

The compositions according to the invention can be formulated into various dosage forms wherein the active ingredients and/or excipients may be present either together (e.g. as an admixture) or as separate components. When the various ingredients in the composition are formulated as a mixture, such composition can be delivered by administering such a mixture. The composition or dosage form wherein the ingredients do not come as a mixture, but come as separate components, such composition/dosage form may be administered in several ways. In one possible way, the ingredients may be mixed in the desired proportions and the mixture is then administered as required. Alternatively, the components or the ingredients (active or inert) may be separately administered (simultaneously or one after the other) in appropriate proportion so as to achieve the same or equivalent therapeutic level or effect as would have been achieved by administration of the equivalent mixture.

Similarly, in the methods according to the invention, the active ingredients disclosed herein may be administered to a subject in several ways depending on the requirements. In some embodiments, the active ingredients are admixed in appropriate amounts and then the admixture is administered separately, the invention further provides for combining separate pharmaceutical compositions in kit form. The kit may comprise one or more separate pharmaceutical compositions, each comprising one or more active ingredients. Each of such separate compositions may be present in a separate container such as bottle, vial, syringes, boxes, bags, and the like. Typically, the kit comprises directions for the administration of the separate components. The kit form is particularly advantageous when the separate components are preferably administered in different dosage intervals. When the active ingredients are administered separately, they may be administered simultaneously or sequentially.

The pharmaceutical composition or the active ingredients according to the present invention may be formulated into a variety of dosage forms. Typical, non-limiting examples of dosage forms include solid, semi-solid, liquid and aerosol dosage forms; such as tablets, capsules, powders, solutions, suspensions, suppositories, aerosols, granules, emulsions, syrups, elixirs and a like.

In general, the pharmaceutical compositions and method disclosed herein are useful in preventing or treating bacterial infections. Advantageously, the compositions and methods disclosed herein are also effective in preventing or treating infections caused by bacteria that are considered to be less or not susceptible to one or more of known antibacterial agents or their known compositions. Some non-limiting examples of such bacteria known to have developed resistance to various antibacterial agents include *Acinetobacter, E. coli, Pseudomonas aeruginosa, Staphylococcus aureus, Enterobacter, Klebsiella, Citrobacter* and a like. Other non-limiting examples of infections that may be prevented or treated using the compositions and/or methods of the invention include: skin and soft tissue infections, febrile neutropenia, urinary tract infection, intraabdominal infections, respiratory tract infections, pneumonia (nosocomial), bacteremia meningitis, surgical, infections etc.

Surprisingly, the compounds, pharmaceutical compositions and methods according to the invention are useful in treatment or prevention of infections caused by resistant bacteria. The compounds, compositions and methods according to the invention are also useful in treatment or prevention of infections caused by bacteria producing one or more beta-lactamase enzymes including those producing extended spectrum beta-lactamase enzymes.

In some embodiments, there is provided a method for preventing or treating a bacterial infection in a subject, said infection being caused by bacteria producing one or more beta-lactamase enzymes, wherein the method comprises administering to said subject a compound of Formula (I). In some other embodiments, there is provided a method for preventing or treating a bacterial infection in a subject, said infection being caused by bacteria producing one or more beta-lactamase enzymes, wherein the method comprises administering to said subject a pharmaceutical composition comprising compound of Formula (I).

In general, the compounds of Formula (I) or a stereoisomer or a pharmaceutically acceptable derivative thereof according to invention are also useful in increasing antibacterial effectiveness of an antibacterial agent in a subject. The antibacterial effectiveness of one or more antibacterial agents may be increased, for example, by co-administering said antibacterial agents or a pharmaceutically acceptable derivative thereof with a compound of Formula (I) or a stereoisomer or a pharmaceutically acceptable derivative thereof according to the invention. In some other embodiments, there are provided methods for increasing antibacterial effectiveness of an antibacterial agent in a subject, said method comprising co-administering said antibacterial agent or a pharmaceutically acceptable derivative thereof with a compound of Formula (I) or a stereoisomer or a pharmaceutically acceptable derivative thereof.

It will be readily apparent to one skilled in the art that varying substitutions and modifications may be made to the invention disclosed herein without departing from the scope and spirit of the invention. For example, those skilled in the art will recognize that the invention may be practiced using a variety of different compounds within the described generic descriptions.

EXAMPLES

The following examples illustrate the embodiments of the invention that are presently best known. However, it is to be understood that the following are only exemplary or illustrative of the application of the principles of the present invention. Numerous modifications and alternative compositions, methods and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Example-1

(2S,5R)-Sulfuric acid mono-[2-(5-azetidin-3-ylmethyl-1,3,4-oxadiazol-2-yl)-7-oxo-1,6-diaza-bicyclo[3.2.1]oct-6-yl]ester

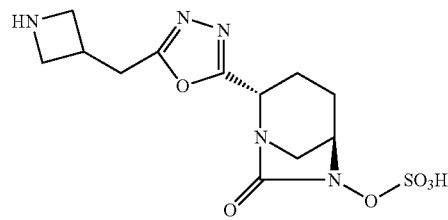 [SMILES: O=C1N2C[C@@H](CC[C@H]2c2nnc(CC3CNC3)o2)N1OS(=O)(=O)O]

Step-1: Preparation of (2S,5R)-2-{N'-[2-(S)-N-tert-butoxycarbonyl-azetidin-2-yl-acetyl]-hydrazino carbonyl}-6-benzyloxy-7-oxo-1,6-diaza-bicyclo[3.2.1]octane To a solution of sodium (2S, 5R)-7-oxo-6-benzyloxy-1,6-diazabicyclo[3.2.1] octane-2-carboxylate (8.45 g, 28.3 mmol) (prepared according to the process disclosed in PCT/IB2013/059264) in water (100 ml) was added 3-(N-tert-butoxycarbonyl-azetidin-3-yl)-acetic acid hydrazide (5.9 g, 25.7 mmol), EDC hydrochloride (7.47 g, 38.6 mmol) and N-hydroxybenzotriazole (3.47 g, 25.7 mmol) at 25° C. to 35° C. under stirring. The reaction mixture was stirred for 18 hours. Precipitated solid was filtered under suction and washed with water (100 ml). It was dried to provide 10.01 g of (2S,5R)-2-{N'-[2-(S)-N-tert-butoxycarbonyl-azetidin-2-yl-acetyl]-hydrazinocarbonyl}-6-benzyloxy-7-oxo-1,6-diaza-bicyclo [3.2.1] octane in 80% yield.

Analysis:
Mass: 486.4 (M−1), for Molecular Formula of $C_{24}H_{33}N_5O_6$;
Purity as determined by HPLC: 89.90%.

Step-2: Preparation of (2S,5R)-2-(5-(N-tert-butoxycarbonylazetidin-3-yl)-methyl-[1,3,4]-oxadiazol-2-yl)-6-benzyloxy-7-oxo-1,6-diaza-bicyclo[3.2.1]octane To a solution of (2S,5R)-2-{N'-[2-(S)-N-tert-butoxycarbonyl-azetidin-2-yl-acetyl]-hydrazinocarbonyl}-6-benzyloxy-7-oxo-1,6-diaza-bicyclo[3.2.1] octane (4 gm, 8.21 mmol) in chloroform (70 ml) was added p-toluenesulfonylchloride (2.34 gm, 12.3 mmol) followed by diisopropylethylamine (4.4 ml, 24.6 mmol). The reaction mixture was heated under stirring at 75° C. for 18 hours. The reaction mixture was concentrated under vacuum and the resulting mass was purified by using silica gel column chromatography, to provide (2S,5R)-2-(5-(N-tert-butoxycarbonylazetidin-3-yl)-methyl-[1,3,4]-oxadiazol-2-yl)-6-benzyloxy-7-oxo-1,6-diaza-bicyclo[3.2.1] octane in 3.3 g quantity in 86% yield as a solid.

Analysis:
Mass: 470.4 (M+1), for Molecular Formula of $C_{24}H_{31}N_5O_5$;
$^1$H NMR: (CDCl$_3$): δ 7.36-7.44 (m, 5H), 5.08 (d, 1H), 4.93 (d, 1H), 4.68-4.71 (m, 1H), 4.10-4.15 (m, 2H), 3.68-3.72 (m, 2H), 3.37 (s, 1H), 3.13-3.15 (m, 2H), 2.90-3.11 (m, 2H), 2.77 (d, 1H), 2.25-2.31 (m, 2H), 2.10-2.19 (m, 1H), 1.87-1.97 (m, 1H), 1.43 (s, 9H).

Step-3: Preparation of (2S,5R)-2-(5-(N-tert-butoxycarbonylazetidin-3-yl)-methyl-[1,3,4]-oxadiazol-2-yl)-6-hydroxy-7-oxo-1,6-diaza-bicyclo[3.2.1]octane To the solution of (2S,5R)-2-(5-(N-tert-butoxycarbonylazetidin-3-yl)-methyl-[1,3,4]-oxadiazol-2-yl)-6-benzyloxy-7-oxo-1,6-diaza-bicyclo[3.2.1] octane (3.3 g, 7.0 mmol) in methanol (35 ml) was subjected to catalytic hydrogenolysis using 10% palladium on charcoal (350 mg) under atmospheric hydrogen gas pressure at 25° C. to 35° C. for 2 hours. The reaction mixture was filtered through celite bed and was washed with methanol (30 ml). The filtrate was concentrated under vacuum below 35° C. to provide 2.7 g of (2S,5R)-2-(5-(N-tert-butoxycarbonylazetidin-3-yl)-methyl-[1,3,4]-oxadiazol-2-yl)-6-hydroxy-7-oxo-1,6-diaza-bicyclo [3.2.1] octane, which was used immediately for the next reaction.

Analysis:
Mass: 378.4 (M−1), for Molecular Formula of $C_{17}H_{25}N_5O_5$.

Step-4: Preparation of tetrabutylammonium salt of (2S,5R)-2-(5-(N-tert-butoxycarbonylazetidin-3-yl)-methyl-[1,3,4]-oxadiazol-2-yl)-6-sulphooxy-7-oxo-1,6-diaza-bicyclo[3.2.1]octane To a solution of (2S,5R)-2-(5-(N-tert-butoxycarbonylazetidin-3-yl)-methyl-[1,3,4]-oxadiazol-2-yl)-6-hydroxy-7-oxo-1,6-diaza-bicyclo[3.2.1] octane (2.7 gm, 7.12 mmol) in dichloromethane (50 ml) was added triethylamine (5 ml, 35 mmol) followed by sulfur trioxide pyridine complex (2.26 g 14.2 mmol) under stirring at 25° C. to 35° C. The reaction mixture was stirred for 2 hours. To the reaction mixture was added aqueous 0.5 N potassium dihydrogen phosphate solution (100 ml). It was stirred for about 30 minutes and tetrabutyl ammonium hydrogen sulfate (2.17 gm 6.4 mmol) was added. It was stirred for 2 hours. Layers were separated and organic layer was concentrated under vacuum to provide a crude mass, which was purified by silica gel column chromatography to furnish 2.1 g of tetrabutylammonium salt of (2S,5R)-2-(5-(N-tert-butoxycarbonylazetidin-3-yl)-methyl-[1,3,4]-oxadiazol-2-yl)-6-sulphooxy-7-oxo-1,6-diaza-bicyclo[3.2.1] octane as solid in 43% yield.

Analysis:
Mass: 458.3 (M−1), as a free sulfonic acid, for Molecular Formula of $C_{17}H_{25}N_5O_8S$. $N(C_4H_9)_4$;
Purity as determined by HPLC: 94.87%.

Step-5: Preparation of (2S,5R)-sulfuric acid mono-[2-(5-azetidin-3-ylmethyl-[1,3,4]-oxadiazol-2-yl)-7-oxo-1,6-diaza-bicyclo[3.2.1]oct-6-yl]ester To the solution of tetrabutylammonium salt of (2S,5R)-2-(5-(N-tert-butoxycarbonylazetidin-3-yl)-methyl-[1,3,4]-oxadiazol-2-yl)-6-sulphooxy-7-oxo-1,6-diaza-bicyclo [3.2.1] octane (1.0 g, 2.2 mmol) in dichloromethane (5 ml) was charged trifluoroacetic acid (5 ml) with syringe at −10° C. under stirring. The reaction mixture was stirred for 1 hour. The mixture was evaporated under vacuum by maintaining temperature below 35° C., to provide a residue, which was suspended in diethyl ether (25 ml) twice. The suspension was filtered and the solid was suspended further in dichloromethane (50 ml) and stirred for 30 minutes. The suspension was filtered and dried to afford the 310 mg of (2S,5R)-sulfuric acid mono-[2-(5-azetidin-3-ylmethyl-[1,3,4]-oxadiazol-2-yl)-7-oxo-1,6-diaza-bicyclo[3.2.1] oct-6-yl] ester as a solid in 60% yield.

Analysis:
Mass: 358.2 (M−1), for Molecular Formula of $C_{12}H_{17}N_5O_6S$;
$^1$H NMR (DMSO-d6): δ 8.50 (br s, 1H), 8.62 br s, 1H), 4.60 (d, 1H), 4.05 (s, 3H), 3.82-3.84 (m, 1H), 3.21-3.27 (m, 4H), 2.93-2.96 (m, 1H), 2.75 (d, 1H), 2.12-2.17 (m, 1H), 1.96-2.05 (m, 2H), 1.82-1.88 (m, 1H).

The representative compounds of Formula (I)-Compounds 2 to 14 (Table 1) were prepared by using the procedure described in Example-1 and by using corresponding acid hydrazide in the step-1.

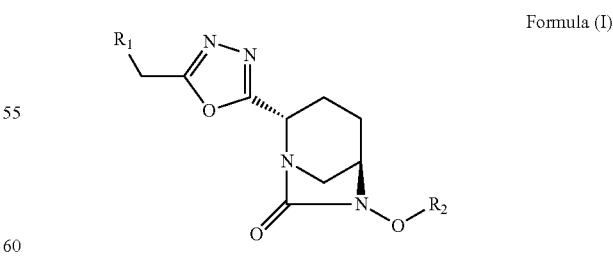

Formula (I)

The sodium salt of the compound of the invention was obtained by loading tetrabutyl ammonium salt as obtained in step-4 of Example-1, on freshly activated Amberlite-IR 120 sodium resin column, and by eluting with tetrahydrofuran water mixture (10:90). The required fractions were concentrated under vacuum to deliver sodium salt of invention.

TABLE 1

Analytical data of compounds of the invention

| Example No. | Heterocyclic acid hydrazide | R₁ | ¹H NMR | Mass (Molecular Formula) |
|---|---|---|---|---|
| 2 | pyrrolidine-N-boc-CH₂CONHNH₂ | pyrrolidine-NH-CH(CH₃) | (DMSO-d6): δ 9.05 (s, 1H), 8.65 (s, 1H), 4.62 (d, 1H), 4.07 (s, 1H), 3.92-3.96 (m, 1H), 3.35-3.44 (m, 3H), 3.20-3.27 (m, 2H), 2.97 (d, 1H), 2.76 (d, 1H), 2.14-2.21 (m, 2H), 1.91-2.06 (m, 2H), 1.82-1.89 (m, 2H), 1.67-1.73 (m, 1H). | 372.1 (M − 1) (C₁₃H₁₉N₅O₆S) |
| 3 | boc-N-piperidine-CH₂CONHNH₂ | HN-piperidine-CH₂ | (DMSO-d6): δ 8.42 (s, 1H), 8.12 (s, 1H), 4.60 (d, 1H), 4.38 (br s, 2H), 4.04 (s, 1H), 3.26 (d, 2H), 2.84-2.96 (m, 4H), 2.71 (d, 1H), 1.96-2.18 (m, 4H), 1.80-1.85 (m, 2H), 1.33-1.43 (m, 2H). | 386.2 (M − 1) (C₁₄H₂₁N₅O₆S) |
| 4 | boc-piperazine-boc-CH₂CONHNH₂ | HN-piperazine-NH-CH₂ | (DMSO-d6) = 9.05 (br s, 3H), 4.61 (d, 1H), 4.09 (s, 1H), 3.80-3.84 (m, 1H), 3.64 (d, 1H), 3.42-3.52 (m, 3H), 3.26-3.38 (m, 2H), 3.00-3.21 (m, 3H), 2.82-2.86 (m, 1H), 2.13-2.25 (m, 1H), 2.00-2.09 (m, 2H), 1.80-1.89 (m, 1H). | 387.3 (M − 1), as free sulfonic acid (C₁₃H₂₁N₆S·C₂O₂F₃) |
| 5 | Ph-CH₂-CONHNH₂ | Ph-CH₂ | (DMSO-d6): δ 7.26-7.39 (m, 5H), 4.61 (d, 1H), 4.31 (s, 2H), 4.05 (s, 1H), 2.92 (d, 1H), 2.71 (d, 1H), 2.10-2.20 (m, 1H), 1.93-2.06 (m, 2H), 1.82-1.91 (m, 1H). | 379.2 (M − 1), as free sulfonic acid (C₁₅H₁₅N₄O₆SNa) |
| 6 | Ph-CH₂CH₂-CONHNH₂ | Ph-CH₂CH₂ | (DMSO-d6): δ 7.13-7.30 (m, 5H), 4.59 (d, 1H), 4.03 (s, 1H), 3.18 (t, 2H), 3.04 (t, 2H), 2.92 (d, 1H), 2.60 (d, 1H), 2.08-2.16 (m, 1H), 1.93-2.05 (m, 2H), 1.76-1.85 (m, 1H). | 393.3 (M − 1), as free sulfonic acid (C₁₆H₁₇N₄O₆SNa) |
| 7 | Ph-CH₂CH₂CH₂-CONHNH₂ | Ph-CH₂CH₂CH₂ | (DMSO-d6): δ 7.25-7.33 (m, 2H), 7.14-7.22 (m, 3H), 4.59 (d, 1H), 4.03 (s, 1H), 2.93 (d, 1H), 2.86 (t, 2H), 2.72 (s, 2H), 2.63-2.68 (m, 2H), 2.12-2.17 (m, 1H), 1.92-2.07 (m, 4H), 1.79-1.90 (m, 1H). | 407.4 (M − 1), as free sulfonic acid (C17H19N4O6SNa) |
| 8 | Ph₂CH-CONHNH₂ | Ph₂CH | (DMS0-d6): δ 7.22-7.40 (m, 10 H), 6.00 (s, 1H), 4.63 (d, 1H), 4.03 (s, 1H), 2.92 (d, 1H), 2.71 (d, 1H), 2.14-2.19 (m, 1H), 1.92-2.04 (m, 2H), 1.78-1.90 (m, 1H). | 455.4 (M − 1), as free sulfonic acid (C₂₁H₁₉N₄O₆SNa) |
| 9 | Ph₂CH-CH₂-CONHNH₂ | Ph₂CH-CH₂ | (DMSO-d6): δ 7.37-7.42 (m, 4H), 7.26-7.29 (m, 4H), 7.15-7.19 (m, 2H), 4.53-4.58 (m, 2H), 3.98 (s, 1H), 3.72-3.74 (m, 2H), 2.80 (d, 1H), 2.27 (d, 1H), 1.55-1.95 (m, 1H). | 487.4 (M − 1), as free sulfonic acid (C₂₂H₂₁N₄O₆SNa) |

TABLE 1-continued

Analytical data of compounds of the invention

| Example No. | Heterocyclic acid hydrazide | $R_1$ | $^1$H NMR | Mass (Molecular Formula) |
|---|---|---|---|---|
| 10 | Cl-C6H4-CH2-CONHNH2 | Cl-C6H4-CH2- | (DMSO-d6): δ 7.32-7.42 (m, 4H), 4.60 (d, 1H), 4.29 (d, 2H), 4.03 (s, 1H), 2.92 (d, 1H), 2.69 (d, 1H), 2.10-2.17 (m, 1H), 1.96-2.05 (m, 2H), 1.80-1.92 (m, 1H). | 413.1 (M − 1), as free sulfonic acid ($C_{15}H_{14}N_4O_6SClNa$) |
| 11 | boc-NH-C6H4-CH2-CONHNH2 | H2N-C6H4-CH2- | (DMSO-d6): δ 9.20 (br s, 3H), 7.40 (d, 2H), 7.24 (d, 2H), 4.59 (d, 1H), 4.32 (s, 2H), 4.03 (s, 1H), 2.92 (d, 1H), 2.68 (d, 1H), 2.10-2.15 (m, 1H), 1.87-2.04 (m, 2H), 1.78-1.90 (m, 1H). | 394.1 (M − 1), ($C_{15}H_{17}N_5O_6S$) |
| 12 | (CH3)2N-C6H4-CH2-CONHNH2 | (CH3)2N-C6H4-CH2- | (DMSO-d6): δ 7.10 (d, 2H), 6.68 (d, 2H), 4.57 (d, 1H), 4.12 (s, 2H), 4.02 (s, 1H), 2.90 (d, 1H), 2.85 (s, 6H), 2.68 (d, 1H), 2.11 (dd, 1H), 1.91-2.02 (m, 2H), 1.78-1.89 (m, 1H). | 422.4 (M − 1), as free sulfonic acid ($C_{17}H_{20}N_5O_6SNa$) |
| 13 | TBDMS-O-C6H4-CH2-CONHNH2 | HO-C6H4-CH2- | (DMSO-d6): δ 9.36 (s, 1H), 7.09 (d, 2H), 6.70 (d, 2H), 4.58 (d, 1H), 4.17 (s, 2H), 4.03 (s, 1H), 2.90 (d, 1H), 2.67 (d, 1H), 2.08-2.17 (m, 1H), 1.92-2.03 (m, 2H), 1.79-1.87 (m, 1H). | 395.3 (M − 1), as free sulfonic acid ($C_{15}H_{15}N_4O_7SNa$) |
| 14 | MeO-C6H4-CH2-CONHNH2 | MeO-C6H4-CH2- | (DMSO-d6): δ 7.23 (d, 2H), 6.89 (d, 2H), 4.58 (d, 1H), 4.20 (s, 2H), 4.03 (s, 1H), 3.72 (s, 3H), 2.91 (d, 1H), 2.66 (d, 1H), 2.10-2.16 (m, 1H), 1.93-2.03 (m, 2H), 1.79-1.88 (m, 1H). | 409.2 (M − 1), as free sulfonic acid ($C_{16}H_{17}N_4O_7SNa$) |

Biological Activity Data

The biological activity of representative compounds according to the invention against various bacterial strains was investigated. In a typical study, overnight grown bacterial cultures were diluted appropriately and inoculated on the agar media containing doubling dilutions of the test compounds. Observations for growth or no growth was performed after 16-20 hours of incubation at 35±2° C. in the ambient air. The overall procedure was performed as per Clinical and Laboratory Standards Institute (CLSI) recommendations, (Clinical and Laboratory Standards Institute (CLSI), Performance Standards for Antimicrobial Susceptibility Testing, 20th Informational Supplement, M 07-A9, Volume 32, No. 2, 2012). Molten Mueller Hinton Agar (BD, USA) containing serial dilutions of each antibacterial agent were poured on to the plates and allowed to solidify. Appropriate suspensions from the freshly grown cultures were prepared in normal saline so that about $10^4$ CFU/spot of the organism was delivered on to the drug containing agar plates using automated multipoint inoculator (Mast, UK). The plates were incubated in Biochemical oxygen demand (BOD) incubator at 37° C. for 18 hours and then examined for growth.

TABLE 2

Antibacterial activity of representative compounds according to the invention (expressed as MICs (mcg/ml))

| Compound | E. Coli NCTC 13353 (CTX-M15, OXA-1) | K. pneumoniae H521 (KPC, SHV, TEM) | K. Pneomoniae S48 (NDM, SHV, TEM) |
|---|---|---|---|
| Imipenem | 0.25 | 16 | 16 |
| Ceftazidime | 32 | >32 | >32 |
| Example 1 | >32 | >32 | >32 |
| Example 2 | >32 | >32 | 32 |
| Example 3 | >32 | >32 | >32 |
| Example 4 | >32 | >32 | >32 |
| Example 5 | 8 | 32 | 8 |
| Example 6 | >32 | >32 | >32 |
| Example 7 | >32 | >32 | 32 |
| Example 8 | >32 | >32 | >32 |
| Example 9 | >32 | >32 | >32 |
| Example 10 | >32 | >32 | >32 |
| Example 11 | >32 | >32 | 32 |
| Example 12 | >32 | >32 | >32 |
| Example 13 | >32 | >32 | >32 |
| Example 14 | >32 | >32 | >32 |

Table 2 details the antibacterial activity of representative compounds according to invention, against various Multi Drug Resistant (MDR) Gram-negative bacterial strains. The strains selected for study included E. coli NCTC 13353 producing CTX-M15 and OXA-1 beta-lactamase enzymes; K. pneumoniae H521 producing KPC, SHV, TEM beta-lactamase enzymes; and K. pneumoniae S48 producing NDM, SHV, TEM beta-lactamase enzymes. The activities are expressed as Minimum Inhibitory Concentrations (MICs) (mcg/ml). The antibacterial activity profile of representative compounds according to invention were compared against known antibacterial agent such as imipenem and ceftazidime. As can be seen, the MIC values for representative compounds of Formula (I) were comparitively higher in comparison to the standards (imipenem and ceftazidime). Therefore, the results of Table 2 suggests that the compounds of invention when used alone exhibited lesser antibacterial activity against the multidrug resistant gram negative strains.

Table 3 details the antibacterial activity of representative compound of Formula (I), sodium salt of (2S,5R)-sulfuric acid mono-[2-(5-benzyl-[1,3,4]-oxadiazol-2-yl)-7-oxo-1,6-diaza-bicyclo[3.2.1] oct-6-yl] ester (Compound of Example 5), against various Multi Drug Resistant (MDR) Gram-negative bacterial strains. The activities are expressed as Minimum Inhibitory Concentrations (MICs) (mcg/ml). The antibacterial activity profile of Compound of Example 5 was compared with avibactam. As can be seen from the data, Compound of Example 5 exhibited antibacterial activity in comparison to avibactam.

TABLE 3

Antibacterial activity of Sodium salt of (2S,5R)-sulfuric acid mono-[2-(5-benzyl-[1,3,4]-oxadiazol-2-yl)-7-oxo-1,6-diaza-bicyclo[3.2.1] oct-6-yl] ester (Compound of Example 5) against various Gram negative organisms

| | MIC (mcg/ml) | |
|---|---|---|
| Organism | Compound of Example 5 | Avibactam |
| E. coli NCTC 13351 | 16 | >64 |
| E. coli NCTC 13352 | 16 | >64 |
| E. coli NCTC 13353 | 8 | 16 |
| E. coli M 49 | >32 | 16 |
| E. coli M 50 | 16 | >64 |
| E. coli 7 MP | 32 | >64 |
| C. frundaii 58 MP | >32 | >64 |
| E. cloacae M 20 | >32 | >64 |
| K. pneumoniae H 521 | 32 | 16 |
| K. pneumoniae H 525 | 16 | 8 |
| K. pneumoniae B 77 | >32 | 32 |
| K. pneumoniae S 21 | >32 | 16 |
| P. aeruginosa PAO1 | >32 | >64 |
| P. aeruginosa ATCC 27853 | >32 | >64 |
| P. aeruginosa R 20 | >32 | >64 |
| P. aeruginosa 2779 | >32 | >64 |

Determination of Enzyme Inhibition Activity:

$IC_{50}$ is concentration of the compound required to inhibit 50% of enzymatic activity. $IC_{50}$ values for various compounds was measured by adding Nitrocefin (100 μM, 5 min) to the preincubated mixture of crude enzyme and the compounds (37° C., 10 minutes). Absorbance was measured at 485 nm by UV-spectrophotometer. The $IC_{50}$ was calculated by plotting absorbance against concentration through Sigmoidal dose response curve using Graph Pad software.

The Table 4 provides the beta-lactamase enzyme inhibition activity of representative compounds of Formula (I), against Multi Drug Resistant Gram-negative bacterial strains expressing various ESBLs. The enzyme inhibition was expressed as $IC_{50}$. As can be seen from the data of Table 4, the beta-lactamase enzyme inhibition values for the compounds according to invention were found to be lower than avibactam and clavulanic acid. The compounds according to invention exhibited potent antibacterial activity against wide variety of bacteria producing Class A, Class C and Class D types of beta-lactamase enzymes. Surprisingly, the representative compounds according to invention exhibit even better than avibactam and clavulanic acid.

TABLE 4

Beta-lactamase enzyme inhibition activity of representative compounds according to invention (expressed as IC50 (μM))

| Example No. | Class A K. pneumoniae ATCC 700603 (SHV 18) | Class C E. coli M50 (CMY/DHA) | Class D A baumannii NCTC 13301 (OXA 23) |
|---|---|---|---|
| Avibactam | 0.098 | 0.146 | 9.735 |
| Clavulanic acid | 0.02 | >10 | >10 |
| Example 1 | 0.027 | 0.402 | 3.947 |
| Example 2 | 0.027 | 0.072 | 12.93 |
| Example 3 | 0.039 | 0.020 | 5.717 |
| Example 4 | 0.027 | 0.021 | 0.410 |
| Example 5 | 0.033 | 0.006 | 0.280 |
| Example 6 | 0.032 | 0.004 | 0.220 |
| Example 7 | 0.040 | 0.004 | 0.115 |
| Example 8 | 0.037 | 0.017 | 0.008 |
| Example 9 | 0.004 | 0.001 | 0.24 |
| Example 10 | — | 0.010 | 0.108 |
| Example 11 | — | 0.013 | 0.108 |
| Example 12 | 0.010 | 0.006 | 0.097 |
| Example 13 | 0.013 | 0.0001 | 0.039 |
| Example 14 | — | 0.013 | 0.080 |

Agar Dilution MIC Determination Method:

Agar dilution MIC was carried out in Muller Hinton Agar (Difco, USA) according to the recommendations of CLSI (M07-A9). In short, the plates were poured with a range of doubling increasing concentration of Ceftazidime and fixed 4 μg/ml compound according to invention containing MHA. The freshly overnight grown cultures were diluted in physiological saline to deliver per spot $10^4$ CFU. The plates were inoculated with a multipoint inoculator (Mast, UK) and incubated at 35° C. for 18 hours. MICs were read as the lowest concentration of drug that completely inhibited visible bacterial growth as per CLSI guidelines. Table-5 provides the result of combination MIC results.

The results of Table 5 show that the MIC values of Ceftazidime in presence of compounds according to the invention (at 4 μg/ml). As shown in Table 5, the MIC value of Ceftazidime was significantly lowered in presence of representative compounds according to the invention. Thus combination of a compound of Formula (I) and an antibacterial agent exhibited good antibacterial activity against highly resistant bacterial strains.

The results of Tables 1 to 5 clearly demonstrate that the representative compounds of Formula (I) exhibited potent beta-lactamase enzyme inhibition against Multi Drug Resistant Gram-negative bacterial strains expressing highly resistant ESBLs. Thus, combination of compounds of Formula (I) with antibacterial agents has tremendous beneficial effect in inhibiting highly resistant bacterial strains demonstrating the noteworthy therapeutic advance in the treatment of infections caused by such pathogens.

TABLE 5

Antibacterial activity of representative compounds according to the invention in combination with Ceftazidime.

| Sr. Compounds | K. pneumoniae ATCC 700606 | E. coli NCTC 13353 | E. coli M 50 | Citrobactor spp 58 MP | K. pneumoniae H521 |
|---|---|---|---|---|---|
| 1. Ceftazidime alone | 32 | 32 | >32 | 16 | >32 |
| 2. Ceftazimime + Example 1 (4 mcg/ml) | 1 | 0.25 | 1 | 0.12 | 2 |
| 3. Ceftazidime + Example 4 (4 mcg/ml) | 1 | 0.25 | 1 | 0.25 | 1 |
| 4. Ceftazidime + Example 5 (4 mcg/ml) | 4 | 0.25 | 4 | 0.5 | 32 |
| 5. Ceftazidime + Example 6 (4 mcg/ml) | 8 | 0.5 | 8 | 4 | >32 |
| 6. Ceftazidime + Example 7 (4 mcg/ml) | 8 | 0.5 | 8 | 4 | >32 |
| 7. Ceftazidime + Example 8 (4 mcg/ml) | 16 | 2 | 32 | 16 | >32 |
| 8. Ceftazidime + Example 9 (4 mcg/ml) | 8 | 4 | 32 | 16 | >32 |
| 9. Ceftazidime + Example 10 (4 mcg/ml) | 8 | 0.25 | 8 | 1 | >32 |
| 10. Ceftazidime + Example 11 (4 mcg/ml) | 4 | 0.25 | 2 | 0.5 | 16 |
| 11. Ceftazidime + Example 12 (4 mcg/ml) | 8 | 1 | 16 | 4 | >32 |
| 12. Ceftazidime + Example 13 (4 mcg/ml) | 4 | 0.5 | 2 | 0.5 | 16 |
| 13. Ceftazidime + Example 14 (4 mcg/ml) | 32 | 0.25 | 8 | 0.5 | >32 |

The invention claimed is:

1. A compound of Formula (I):

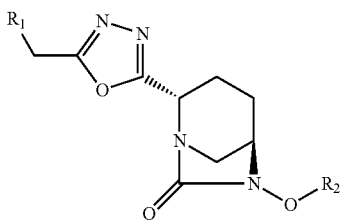

Formula (I)

or a stereoisomer or a pharmaceutically acceptable salt thereof;
wherein:
$R_1$ is:
(a) $C_1$-$C_6$ alkyl substituted with aryl;
(b) aryl optionally substituted with one or more substituents independently selected from $C_1$-$C_6$ alkyl, halogen, CN, $OR_3$, $NR_3R_4$, or $CONR_3R_4$;
$R_2$ is:
(a) $SO_3M$;
$R_3$ and $R_4$ are each independently:
(a) hydrogen, or
(b) $C_1$-$C_6$ alkyl optionally substituted with one or more substitutents independently selected from halogen, CN, OH, O($C_1$-$C_6$ alkyl), NH($C_1$-$C_6$ alkyl), N($C_1$-$C_6$ alkyl)$_2$, CONH($C_1$-$C_6$ alkyl), CON($C_1$-$C_6$ alkyl)$_2$ or aryl;
wherein M is hydrogen or a cation.

2. A compound selected from:
(2S,5R)-sulfuric acid mono-[2-(5-benzyl-[1,3,4]-oxadiazol-2-yl)-7-oxo-1,6-diaza-bicyclo[3.2.1] oct-6-yl] ester;
(2S,5R)-sulfuric acid mono-[2-(5-phenyl-ethyl-[1,3,4]-oxadiazol-2-yl)-7-oxo-1,6-diaza-bicyclo[3.2.1] oct-6-yl] ester;
(2S,5R)-sulfuric acid mono-{2-[5-(3-phenyl-propyl)-[1,3,4]-oxadiazol-2-yl]-7-oxo-1,6-diaza-bicyclo[3.2.1] oct-6-yl} ester;
(2S,5R)-sulfuric acid mono-[2-(5-benzhydryl-[1,3,4]-oxadiazol-2-yl)-7-oxo-1,6-diaza-bicyclo[3.2.1] oct-6-yl] ester;
(2S,5R)-sulfuric acid mono-{2-[5-(2,2-diphenyl-ethyl)-[1,3,4]-oxadiazol-2-yl]-7-oxo-1,6-diaza-bicyclo[3.2.1] oct-6-yl} ester;
(2S,5R)-sulfuric acid mono-{2-[5-(4-chloro-benzyl)-[1,3,4]-oxadiazol-2-yl]-7-oxo-1,6-diaza-bicyclo[3.2.1] oct-6-yl} ester;
(2S,5R)-sulfuric acid mono-{2-[5-(4-amino-benzyl)-[1,3,4]-oxadiazol-2-yl]-7-oxo-1,6-diaza-bicyclo[3.2.1] oct-6-yl} ester;
(2S,5R)-sulfuric acid mono-{2-[5-(4-dimethylamino-benzyl)-[1,3,4]-oxadiazol-2-yl]-7-oxo-1,6-diaza-bicyclo[3.2.1] oct-6-yl} ester;
(2S,5R)-sulfuric acid mono-{2-[5-(4-hydroxy-benzyl)-[1,3,4]-oxadiazol-2-yl]-7-oxo-1,6-diaza-bicyclo[3.2.1] oct-6-yl} ester;
(2S,5R)-sulfuric acid mono-{2-[5-(4-methoxy-benzyl)-[1,3,4]-oxadiazol-2-yl]-7-oxo-1,6-diaza-bicyclo[3.2.1] oct-6-yl} ester;
or a stereoisomer or a pharmaceutically acceptable salt thereof.

3. A compound is selected from:
sodium salt of (2S,5R)-sulfuric acid mono-[2-(5-benzyl-[1,3,4]-oxadiazol-2-yl)-7-oxo-1,6-diaza-bicyclo[3.2.1] oct-6-yl] ester;
sodium salt of (2S,5R)-sulfuric acid mono-[2-(5-phenyl-ethyl-[1,3,4]-oxadiazol-2-yl)-7-oxo-1,6-diaza-bicyclo [3.2.1] oct-6-yl] ester;
sodium salt of (2S,5R)-sulfuric acid mono-{2-[5-(3-phenyl-propyl)-[1,3,4]-oxadiazol-2-yl]-7-oxo-1,6-diaza-bicyclo[3.2.1] oct-6-yl} ester;
sodium salt of (2S,5R)-sulfuric acid mono-[2-(5-benzhydryl-[1,3,4]-oxadiazol-2-yl)-7-oxo-1,6-diaza-bicyclo [3.2.1] oct-6-yl] ester;

sodium salt of (2S,5R)-sulfuric acid mono-{2-[5-(2,2-diphenyl-ethyl)-[1,3,4]-oxadiazol-2-yl]-7-oxo-1,6-diaza-bicyclo[3.2.1] oct-6-yl} ester;

sodium salt of (2S,5R)-sulfuric acid mono-{2-[5-(4-chloro-benzyl)-[1,3,4]-oxadiazol-2-yl]-7-oxo-1,6-diaza-bicyclo[3.2.1] oct-6-yl} ester;

sodium salt of (2S,5R)-sulfuric acid mono-{2-[5-(4-amino-benzyl)-[1,3,4]-oxadiazol-2-yl]-7-oxo-1,6-diaza-bicyclo[3.2.1] oct-6-yl} ester;

sodium salt of (2S,5R)-sulfuric acid mono-{2-[5-(4-dimethylamino-benzyl)-[1,3,4]-oxadiazol-2-yl]-7-oxo-1,6-diaza-bicyclo[3.2.1] oct-6-yl} ester;

sodium salt of (2S,5R)-sulfuric acid mono-{2-[5-(4-hydroxy-benzyl)-[1,3,4]-oxadiazol-2-yl]-7-oxo-1,6-diaza-bicyclo[3.2.1] oct-6-yl} ester;

sodium salt of (2S,5R)-sulfuric acid mono-{2-[5-(4-methoxy-benzyl)-[1,3,4]-oxadiazol-2-yl]-7-oxo-1,6-diaza-bicyclo[3.2.1] oct-6-yl} ester;

or a stereoisomer thereof.

4. A pharmaceutical composition comprising a compound of Formula (I) according to claim 1 and one or more pharmaceutically acceptable excipients.

5. The pharmaceutical composition according to claim 4, wherein a compound of Formula (I) is (2S,5R)-sulfuric acid mono-{2-[5-(4-hydroxy-benzyl)-[1,3,4]-oxadiazol-2-yl]-7-oxo-1,6-diaza-bicyclo[3.2.1] oct-6-yl} ester or a stereoisomer or a pharmaceutically acceptable salt thereof.

6. The pharmaceutical composition according to claim 4, wherein the pharmaceutical composition further comprises at least one beta-lactamase inhibitor, or a pharmaceutically acceptable salt thereof.

7. The pharmaceutical composition according to claim 6, wherein the beta-lactamase inhibitor is selected from the group consisting of sulbactam, tazobactam, clavulanic acid, avibactam, and a pharmaceutically acceptable salt thereof.

8. The pharmaceutical composition according to claim 4, wherein the pharmaceutical composition further comprises at least one antibacterial agent, or a pharmaceutically acceptable salt thereof.

9. The pharmaceutical composition according to claim 8, wherein the antibacterial agent is selected from a group consisting of aminoglycosides, ansamycins, carbacephems, cephalosporins, cephamycins, lincosamides, lipopeptides, macrolides, monobactams, nitrofurans, penicillins, penems, carbapenems, polypeptides, quinolones, sulfonamides, tetracyclines, oxazolidinone and beta-lactam antibacterial agents.

10. The pharmaceutical composition according to claim 8, wherein the antibacterial agent is a cephalosporin antibiotic selected from the group consisting of cephalotin, cephaloridine, cefaclor, cefadroxil, cefamandole, cefazolin, cefalexin, cefradine, ceftizoxime, cefoxitin, cephacetrile, cefotiam, cefotaxime, cefsulodin, cefoperazone, cefmenoxime, cefmetazole, cepfaloglycin, cefonicid, cefodizime, cefpirome, ceftazidime, ceftriaxone, cefpiramide, cefbuperazone, cefozopran, cefepime, cefoselis, cefluprenam, cefuzonam, cefpimizole, cefclidin, cefixime, ceftibuten, cefdinir, cefpodoxime auxetil, cefpodoxime proxetil, cefteram pivoxil, cefetamet pivoxil, cefcapene pivoxil, cefditoren pivoxel, cefuroxime, cefuroxime auxetil, loracarbacef, ceftaroline, ceftolozane, and latamoxef.

11. The pharmaceutical composition according to claim 8, wherein the pharmaceutical composition comprises: (a) (2S,5R)-sulfuric acid mono-{2-[5-(4-hydroxy-benzyl)-[1,3,4]-oxadiazol-2-yl]-7-oxo-1,6-diaza-bicyclo[3.2.1] oct-6-yl} ester, or a stereoisomer or a pharmaceutically acceptable salt thereof, and (b) at least one antibacterial agent selected from cefepime, cefpirome, ceftaroline, ceftazidime, ceftalozane or a pharmaceutically acceptable salt thereof.

12. A method for treating a bacterial infection in a subject, wherein said method comprises administering to said subject a compound according to claim 1.

13. A method for treating a bacterial infection in a subject, wherein said method comprises administering to said subject a pharmaceutical composition according to claim 4.

14. A method for preventing or treating a bacterial infection in a subject, wherein said method comprises administering to said subject: (a) a compound according to claim 1, and (b) at least one beta-lactamase inhibitor or a pharmaceutically acceptable salt thereof.

15. A method for preventing or treating a bacterial infection in a subject, wherein said method comprises administering to said subject: (a) a compound according to claim 1, and (b) at least one antibacterial agent or a pharmaceutically acceptable salt thereof.

16. The method for preventing or treating a bacterial infection in a subject according to claim 15, wherein the said method comprises administering to said subject: (a) (2S,5R)-sulfuric acid mono-{2-[5-(4-hydroxy-benzyl)-[1,3,4]-oxadiazol-2-yl]-7-oxo-1,6-diaza-bicyclo[3.2.1] oct-6-yl} ester, and (b) at least one antibacterial agent selected from cefepime, cefpirome, ceftaroline, ceftazidime, ceftalozane, or a pharmaceutically acceptable salt thereof.

17. A process for the preparation of a compound of Formula (I) according to claim 1, Formula (I)

wherein, $R_1$ is:
(a) $C_1$-$C_6$ alkyl substituted with aryl;
(b) aryl optionally substituted with one or more substituents independently selected from $C_1$-$C_6$ alkyl, halogen, CN, $OR_3$, $NR_3R_4$, or $CONR_3R_4$;

$R_2$ is:
(a) $SO_3M$, $R_3$ and $R_4$ are each independently:
(a) hydrogen, or
(b) $C_1$-$C_6$ alkyl optionally substituted with one or more substitutents independently selected from halogen, CN, OH, O($C_1$-$C_6$ alkyl), NH($C_1$-$C_6$ alkyl), N($C_1$-$C_6$ alkyl)$_2$, CONH($C_1$-$C_6$ alkyl), CON($C_1$-$C_6$ alkyl)$_2$, or aryl or heteroaryl;

wherein M is hydrogen or a cation;

wherein said process comprises:
(a) reacting a compound of Formula (Ia) with $R_1CONHNH_2$ (Ib) in presence of coupling agent to obtain a compound of Formula (Ic);

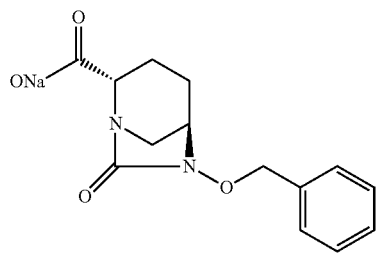

(Ia)

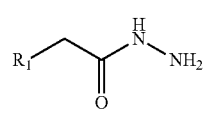

(Ib)

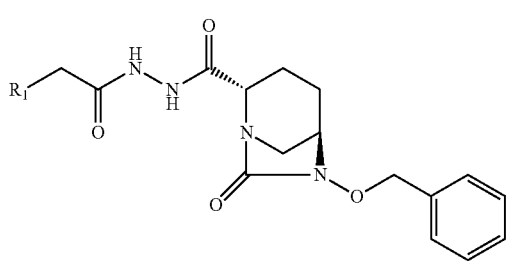

(Ic)

(b) cyclizing a compound of Formula (Ic) to obtain a compound of Formula (Id);

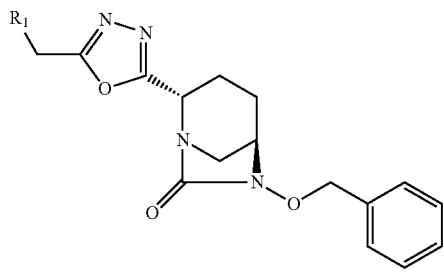

(Id)

(c) hydrogenolysis of a compound of Formula (Id) to obtain a compound of Formula (Ie);

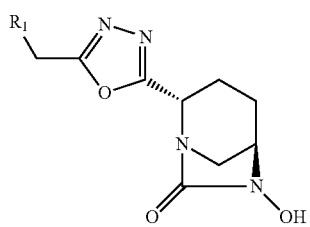

(Ie)

(d) sulfonating a compound of Formula (Ie), followed by the treatment with tetrabutyl ammonium hydrogen sulfate to obtain a compound of Formula (If); and

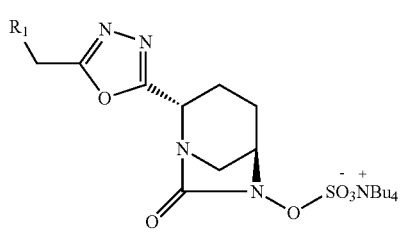

(If)

(e) converting a compound of Formula (If) with trifluoroacetic acid obtain a compound of Formula (I) where M is hydrogen or by optional salt formation to form a compound of Formula (I) where M is a cation.

18. The process according to claim 17, wherein the coupling agent in step (a) is selected from 1-ethyl-3-(3-dimethylaminopropyl)carbodiimide hydrochloride, 1-hydroxybenzotriazole, dicyclohexyl carbodiimde or pivalyl chloride.

19. The process according to claim 17, wherein the sulfonation in step (d) is carried in presence of sulfur trioxide-pyridine complex or sulfur trioxide-N, N-dimethylformamide complex.

* * * * *